US012044759B2

(12) United States Patent
Popescu

(10) Patent No.: US 12,044,759 B2
(45) Date of Patent: Jul. 23, 2024

(54) TOROIDAL SYSTEM CONFIGURATION FOR DEDICATED MRI SCANNERS

(71) Applicant: Siemens Healthcare GmbH, Erlangen (DE)

(72) Inventor: Stefan Popescu, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 104 days.

(21) Appl. No.: 17/103,078

(22) Filed: Nov. 24, 2020

(65) Prior Publication Data

US 2021/0156936 A1 May 27, 2021

Related U.S. Application Data

(60) Provisional application No. 62/941,115, filed on Nov. 27, 2019, provisional application No. 62/941,210, filed on Nov. 27, 2019.

(51) Int. Cl.
*A61B 5/00* (2006.01)
*A61B 3/10* (2006.01)
(Continued)

(52) U.S. Cl.
CPC .......... *G01R 33/34053* (2013.01); *A61B 3/10* (2013.01); *A61B 5/0035* (2013.01);
(Continued)

(58) Field of Classification Search
CPC ............ G01R 33/34053; G01R 33/307; G01R 33/34084; G01R 33/4812; G01R 33/5635;
(Continued)

(56) References Cited

U.S. PATENT DOCUMENTS 5,664,569 A * 9/1997 Damadian .............. A61B 5/055
600/421
6,198,962 B1 * 3/2001 Su ...................... G01R 33/3678
600/422
(Continued)

FOREIGN PATENT DOCUMENTS

EP 3736590 A1 11/2020
EP 3736591 A1 11/2020
(Continued)

OTHER PUBLICATIONS

European Search Report dated Apr. 23, 2021, Application No. 20206872.2 (includes appendix with translations of discussed references).
(Continued)

*Primary Examiner* — Dixomara Vargas
*Assistant Examiner* — Gabriel Victor Popescu
(74) *Attorney, Agent, or Firm* — Banner & Witcoff Ltd.

(57) ABSTRACT

A magnetic resonance imaging system can include a basic field magnetic arrangement for generating a main magnetic field and a number of spatially separated imaging regions, the basic field magnetic arrangement including several spatially separated magnet segments, in order to generate segment magnetic fields with a defined segment field direction, at least two of the spatially separated magnet segments being configured in a way that their defined segment field directions are running in an angular fashion to each other so that the segment magnetic fields result in a main magnetic field which has the form of toroid, where the magnetic resonance imaging system is designed to be adapted to MR imaging of dedicated body or organ parts of a patient.

18 Claims, 21 Drawing Sheets

(51) Int. Cl.
  *A61B 5/055* (2006.01)
  *A61B 6/03* (2006.01)
  *A61N 5/10* (2006.01)
  *G01R 33/30* (2006.01)
  *G01R 33/34* (2006.01)
  *G01R 33/48* (2006.01)
  *G01R 33/563* (2006.01)

(52) U.S. Cl.
  CPC .......... *A61B 5/0036* (2018.08); *A61B 5/0042* (2013.01); *A61B 5/0044* (2013.01); *A61B 5/055* (2013.01); *A61B 5/4312* (2013.01); *A61B 5/4381* (2013.01); *A61B 5/4528* (2013.01); *A61B 5/4547* (2013.01); *A61B 6/032* (2013.01); *A61N 5/1049* (2013.01); *G01R 33/307* (2013.01); *G01R 33/34084* (2013.01); *G01R 33/4812* (2013.01); *G01R 33/5635* (2013.01); *A61N 2005/1055* (2013.01)

(58) Field of Classification Search
  CPC ............ G01R 33/4808; G01R 33/3806; A61B 5/0036; A61B 3/10; A61B 5/0035; A61B 5/0042; A61B 5/0044; A61B 5/055; A61B 5/4312; A61B 5/4381; A61B 5/4528; A61B 5/4547; A61B 6/032; A61B 3/14; A61B 5/4064; A61B 5/407; A61B 2562/04; A61B 2562/046; A61B 6/12; A61B 6/4417; A61N 5/1049; A61N 2005/1055; A61N 5/1065
  See application file for complete search history.

(56) References Cited

U.S. PATENT DOCUMENTS

| | | | |
|---|---|---|---|
| 6,591,127 | B1 | 7/2003 | McKinnon |
| 2003/0103597 | A1 | 6/2003 | Sklebitz |
| 2003/0110564 | A1* | 6/2003 | Yoshinto ............ G01R 33/3806 5/601 |
| 2012/0265050 | A1* | 10/2012 | Wang .................... A61B 6/485 600/411 |
| 2018/0015306 | A1* | 1/2018 | Maurer, Jr. ............ A61B 6/025 |
| 2019/0076080 | A1* | 3/2019 | Prado .................... A61B 5/055 |
| 2019/0274649 | A1 | 9/2019 | Fahrig et al. |
| 2020/0355764 | A1 | 11/2020 | Popescu |
| 2020/0355771 | A1 | 11/2020 | Popescu et al. |

FOREIGN PATENT DOCUMENTS

| | | | |
|---|---|---|---|
| JP | S61159950 A | | 7/1986 |
| JP | H10234704 A | * | 9/1998 ............. A61B 5/055 |
| JP | H10234704 A | | 9/1998 |
| JP | 2003102699 A | | 4/2003 |
| KR | 20150049316 A | | 5/2015 |

OTHER PUBLICATIONS

European Search Report dated Sep. 6, 2021, Application No. 20206872.2.

* cited by examiner

TOROIDAL SYSTEM CONFIGURATION FOR DEDICATED MRI SCANNERS

CROSS REFERENCE TO RELATED APPLICATIONS

This patent application claims priority to, and the benefit of: U.S. Provisional Patent Application No. 62/941,210, filed Nov. 27, 2019; and U.S. Provisional Patent Application No. 62/941,115, filed Nov. 27, 2019, each of which is incorporated herein by reference in its entirety.

BACKGROUND

Field

The disclosure describes a toroidal system configuration for dedicated MRI scanners (MRI: Magnetic resonance imaging) and especially parallel MRI scanners with synchronous operation, including for an MRI-system with two or more imaging regions, and such MRI-system.

Related Art

Magnetic resonance ("MR") technology is a known technology which can be used to generate images of the interior of an object under examination. In simplified terms, for this purpose, the object under examination is positioned in a magnetic resonance device in a comparatively strong static, homogeneous basic magnetic field, also known as the B0 field with field strengths of 0.2 Tesla to 7 Tesla ("T") and more so that the nuclear spins of the object orient along the basic magnetic field. To trigger nuclear spin resonances, high-frequency excitation pulses (HF pulses) are irradiated into the object under examination, the triggered nuclear spin resonances are measured as so-called k-space data and used as the basis for the reconstruction of MR images or the determination of spectroscopy data. For spatial encoding of the measured data, rapidly switched magnetic gradient fields are superimposed on the basic magnetic field. The recorded measured data is digitized and stored in a k-space matrix as complex values. An associated MR image can be reconstructed from the k-space matrix populated with such values, for example by means of a multidimensional Fourier transformation.

The most serious problems occur with regard to the extensive stray magnetic fields around these scanners. In order to cope with this problem and avoid accidents and damage, the hospital administration must delineate a strictly controlled area within and in the vicinity of the MRI examination rooms by limiting the access of people and equipment. Damage can occur if metallic or magnetic parts are attracted by the strong magnets of the MRI scanner and accelerated in the direction of the scanner volume.

Traditional MRI scanners employ a solenoidal type superconducting magnet, while the patient is placed inside the bore of the MRI scanner during the imaging session. Such scanner design confines the patient and limits the accessibility to the patient's body for the medical staff, e.g. to carry out an interventional or therapeutic procedure guided by real-time MR imaging. Another problem is, that the MRI scanners, which use a solenoid-magnet design, "enclose" patients in a narrow patient tunnel, which in particular can cause claustrophobia. This claustrophobia may be so strong in some patients that no MRI scan can be performed. Moreover, due to the narrowness of the examination tunnel, the access of the medical staff to the patient is severely restricted, which is unfavorable for interventional or therapeutic procedures, in particular with regard to real-time MRI imaging.

Typically, MRI scanners use a self-shielded, solenoid-type superconducting magnet to reduce the strength of the leakage magnetic field, resulting from the coil of the basic field magnet. An actively shielded basic field magnet is much more expensive than an unshielded one. In addition, the shield coils reduce the efficiency of the basic magnetic field that can be used for measurements in an examination tunnel. Active shielded magnets have a larger diameter (about 220 cm) than unshielded magnets (about 145 cm).

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
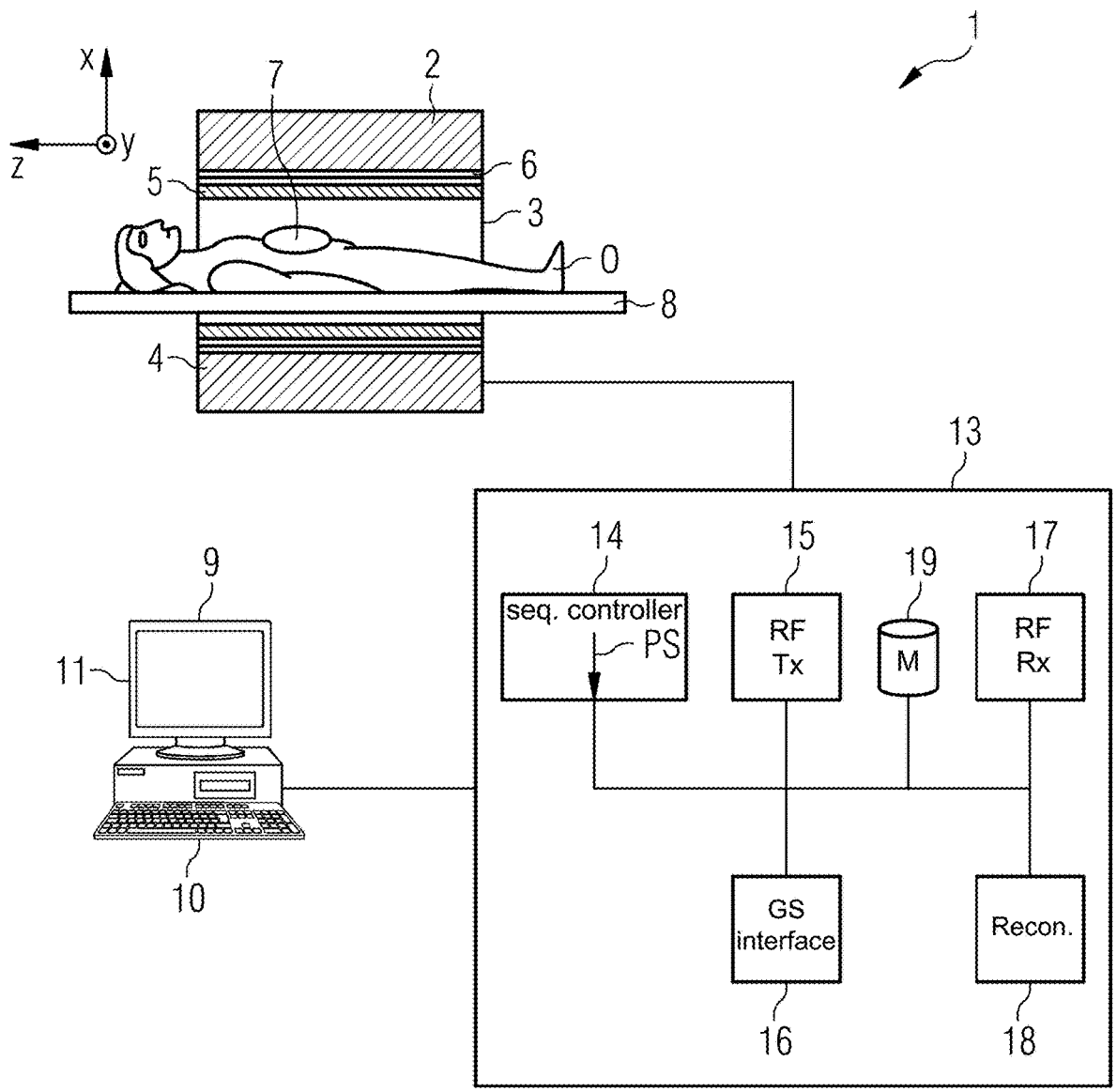
FIG. 1 shows a simplified Magnetic resonance imaging (MRI) system.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to improve the known MRI-systems to facilitate an improved MRI-system, and especially to present a design of a dedicated MR system architecture for imaging a certain body region of the patient. Further preferred objects are MRI-systems, having a lower cost position, are especially designed for the imaging of the respective body region and show the required easy-of-use due to the lack of trained operating personal.

A magnetic resonance imaging (MRI) system according to the disclosure comprises a basic field magnetic arrangement (i.e. a main magnetic field generation unit) for generating a main magnetic field and a number of (one single or multiple) spatially separated imaging regions (can also be designated as "measurement stations"). The basic field magnetic arrangement comprises several spatially separated magnet segments, in order to generate segment magnetic fields with a defined segment field direction or actually a segmented magnetic field with a defined field direction for each segment. At least two of the spatially separated magnet segments are configured in a way that their defined segment field directions are running in an angular fashion to each other, i.e. that their magnetic field directions are linked in an angular fashion to each other, so that the segment magnetic fields (the chained magnetic fields) result in a main magnetic field which has the form of toroid. The magnetic resonance imaging system is designed to be adapted to MR imaging of dedicated body or organ parts of a patient, what means that it is mechanically and/or magnetically designed for that special imaging.

Regarding the expression "imaging region", there are several designations that could be used alternatively, e.g. "imaging volume", "examination area", "examination region", "patient hosting volume or "measurement station". In addition, a measurement could also be designated as a "scan", since the measurement is achieved in MRI with scanning a patient.

It should be noted that all these features pertain to the MRI scanner of the MRI system. Although the MRI system is often designated also as "MRI scanner", it could be advantageous for understanding to regard the MRI system as an apparatus that comprises the MRI scanner, and the MRI scanner as a component of the MRI system, comprising the magnets and space for examinations (imaging regions). Thus, the above combination of features could also define an MRI scanner instead of the whole system (because all features concern elements of the MRI scanner as said above).

Part of the disclosure is the use of a toroidal main magnetic field for a measurement in the context of magnetic resonance tomography, respectively in an MRI-system. Since magnetic fields are not solid, "toroidal" in this context means that there is a magnetic field with circulating field lines wherein at least the shape of the region of the field that can be used for MRI measurements is toroidal. Usually, there is a point in the middle of the field, where the resulting field strength is zero. However, looking at the "usable field" it usually has a "hole" in its center, where the field is too weak to be used for MRI. In addition to essentially circular toroidal magnetic fields themselves, the expression "toroidal" here also comprises, other self-contained magnetic fields, which have the shape of an ellipse, a rectangle with have rounded corners or a shape made up of circular segments and "inserted" straight passages.

In an exemplary embodiment, the MRI system is specifically adapted for one or more of the following MR imaging purposes:
  Cardiac imaging of a heart of a patient
  Mammography imaging of a breast of a patient, especially in a standing position
  Neurological imaging of a brain or spine of a patient
  Urological imaging of a prostate of a patient
  Orthopedics imaging of joints (e.g. knee, shoulder, elbow) of a patient
  Ophthalmologic imaging of an eye of a patient
  Dental imaging of the jaw/teeth of a patient
  MR-guided radiotherapy (i.e. radiation therapy)
  Interventional radiology.

This means especially, that the dimensions and/or the mechanical setup of the MRI scanner is specially designed for the respective purpose.

As said above, in an exemplary embodiment, an MRI system comprises a magnetic resonance imaging scanner, a controller to control this scanner, and also control image acquisition, image reconstruction, and auxiliary devices, e.g. transformers to power the magnetic environment. Usually, the MRI scanner comprises the main magnetic field system (that may also be called "main magnetic field unit").

Thus, the toroidal MRI system (or more accurately: the MRI scanner) comprises a main magnetic field system with multiple spatially separated magnet segments, which each generate a respective main magnetic field. The respective main magnetic fields of the multiple magnet segments are aligned (linked) in an angular fashion to (with) each other so that the whole main magnetic field has the form of a "toroid". For example, the magnet segments are aligned (arranged) in a star-shaped fashion.

The toroidal magnet could be an electromagnet for low-field MRI (0.01 to 0.2 T) or a superconducting magnet for high-field MRI (from 0.1, especially 0.5, to 3 T). The spherical homogeneity volume is part of the toroidal magnetic field having parallel field lines at least within the imaging region (imaging volume). This toroidal magnetic field is produced by the current following into the field generating coils. Such toroidal magnet solutions providing multiple imaging regions are known from the EP patent application Nr. 19173594.3. This EP patent application is hereby incorporated by reference.

One advantage of using toroidal magnet systems for dedicated practitioner MRI scanners is that such magnet configurations minimize the stray field and eliminate the need for active shielding coils, which makes these magnets also even more efficient and cost effective. This allows compact siting of the MRI scanners, even possible directly in the doctor's office without having to install them in a separate examination room.

According to a preferred embodiment of the MRI system at least one imaging region is V-shaped (i.e. wedge-shaped).

In an exemplary embodiment, the magnet segments can be aligned (arranged) in a star-shaped fashion. The idea is to insert the organ to be imaged (e.g. heart, jaw, breast or else) in the imaging volume (i.e. the imaging region), which is defined in at least one cavity of the (toroidal) MRI system. With magnet segments aligned (arranged) in a star-shaped fashion, the imaging region between two magnet segments is V-shaped inside the opening angle of the magnet segments. In particular, the MRI-system can be designed such that the toroidal magnet provides multiple imaging regions, especially for simultaneous operation. Applications of such parallel scanning can be screening examinations, possibly even in the waiting area of a practice or hospital, or other mass patient scanning purposes.

However, the system can also only provide a single imaging region, i.e. only one cavity is provided to position the organ to be imaged in.

In an exemplary embodiment, an angular coverage of an imaging region (of a single, two, three or more, depending on the size and opening angle) can preferably be between 45° and 90° degrees, in particular between 60° and 90° degrees. In an exemplary embodiment, the maximum opening angle of the imaging region is not bigger than 120°, especially said 90° or less, due to the needed homogeneity of the main magnetic field. However, to offer an advantageous space for a patient, especially against claustrophobia or for additional interventions, the opening angle should be bigger than 30°, especially said 45° or more. Such open MRI scanner solution using a toroid magnet and one imaging region could be called "PacMan" MRI scanner, due to the similarity with the protagonist of the Pac-Man arcade game, developed and released by Namco in 1980.

The system can be adapted for different body organs, which may include the changing (readjustment) of shim irons of the magnet. The extension of the magnet and field generating coils along a symmetry axis can be set according to the target application. For example, a dental scanner will have an axial extension along the symmetry axis of preferably 20 cm, or in-between 15 cm and 30 cm. For prostate scanner the extension could be in-between 15 cm and 30 cm. For cardiac imaging the scanner extension can be in-between 30 cm and 60 cm.

In an exemplary embodiment, the magnet field system comprises multiple field generating coils (i.e. the magnet segments of the magnet field system), the coils preferably having a planar distribution of wires optimized such that the generated magnetic field B0 has parallel lines and it is homogenous enough at least for the imaging region contain the patient, e.g. the brain or a dental organ.

It is preferred that gradient coils and/or RF coils are built into the magnet enclosure of the MRI scanner of the MRI system. Alternatively or additionally, it is preferred that local gradient coils and other local coils are used in an imaging region, e.g. wherein a headrest attached to a patient chair or -bed hosts a local gradient coil and/or a local shim coil and/or RF head-coils. Furthermore, in a preferred wedge-shaped imaging region, a V-shaped planar gradient coil (i.e. a V-shaped coil arrangement) is preferred.

Preferred is a MRI system according to the disclosure (a (toroidal) MRI scanner) designed for dental imaging. The field strength is typically 0.1 T to 3 T and the jaw of the patient is positioned in one of the imaging regions (cavities) of the toroidal magnet of the dental MRI scanner. There can be one V-shaped imaging region or multiple imaging regions.

It is preferred that the size of the MRI scanner is such that the imaging region does not exceed a diameter of 50 cm, and is especially smaller than 30 cm. However, the diameter of the imaging region should be bigger than 5 cm, especially bigger than 10 cm to acquire suitable dental images.

A preferred MRI system is designed such, that a patient can stand and/or sit and/or lie on the back during imaging. To arrange the patient in the imaging region, it is preferred that the (toroidal) MRI scanner of the MRI system can be moved towards the patient from the front, e.g. using a hinge mechanism which is fixed to a ceiling of a treatment room. Alternatively or additionally, the patient can be moved to the imaging region, e.g. by moving a patient bed or chair accordingly. Alternatively, the MRI scanner is designed such, that the patient can lie in a predefined position, e.g. on the back of his head, in the cavity of the MRI scanner, especially wherein at least a region of the patient that is to be examined (e.g. the back of the head) rests in a center part of the magnet field system or at least facing the center part of the magnet field system.

It is preferred to use additional positioning means, such as a conventional mouth fixture of panoramic X-ray dental imaging, in order to minimize or avoid motion during scanning.

In order to increase patient comfort, the patient can especially wear stereo goggles during imaging. Alternatively, small openings can be installed in the body of the MRI scanner so that the patient can see through those openings. This minimizes claustrophobic feelings.

A MRI system according to an exemplary embodiment of the disclosure (a (toroidal) MRI scanner) is designed for examinations of the group head imaging, cardiac imaging, spine imaging and prostate imaging. The field strength is typically 0.1 T to 3 T, preferably 0.5 T for cardiac imaging or 1.5 T or 3 T for prostate imaging. A patient is typically sitting on a chair or lying on a bed, wherein the headrest attached to the patient chair or patient bed preferably could host a local gradient coil, and/or a local shim coil and/or as well as the RF head-coils.

It is preferred that the size of the MRI scanner is such that the imaging region covers the region of interest, wherein the diameter of the imaging region should be bigger than 10 cm, especially bigger than 20 cm to acquire suitable images.

For cardiac or abdominal imaging, the patient thorax is positioned within one of the imaging regions (cavities or imaging slots) of the MRI scanner. In an exemplary embodiment, the patient rest, chair or bed, is elevated such that to position the organ of interest within the magnet FOV in the respective imaging regions.

For spine imaging, in an exemplary embodiment, the patient sits on a chair or stands while leaning upright and against a backrest with the backrest closest to the symmetry axis of the magnet.

For prostate imaging it is preferred that the patient sits on a chair. Especially, special prostate coils are integrated into the patient chair. However, for interventional prostate MRI another scanner architecture that is described in the following may be more appropriate.

For interventional breast imaging, a scanner configuration as described above is preferred. For mammography screening applications, a V-shaped imaging region, e.g. of a star shaped arrangement of magnet segments, will better fit the clinical needs of scanning as many as possible patients in given time. Alternatively, the patient pose within the imaging region (imaging slot) could be such that the female patient is sitting on a chair while facing the vertical symmetry axis of the scanner. The patient could also stand while facing one separation wall of the imaging region, that is with the shoulders line parallel to the local X-axis (pointing to the outside) of the imaging region.

Preferred is a MRI system according to the disclosure (with a (toroidal) MRI scanner) designed for Musculoskeletal imaging (MSK imaging, e.g. knee, elbow or shoulder). The open configuration of the MRI system enables easy kinematic examinations of joints of the patient, i.e. imaging the joint of the patient in motion. It is preferred that the patient sits or stands during examination, depending on which imaging setup for the patient's joint is desired.

As said above, a preferred MRI system comprises at least one V-shaped imaging region, i.e. the respective imaging region between two magnet segments is V-shaped and is formed inside the opening angle of these magnet segments. In particular, an advantageous MRI-system is designed that comprises at least one V-shaped imaging region (patient hosting volume) having a spherical field-of-view FOV that is confining a static magnetic field B0 having parallel field lines emerging out of the magnet faces.

It is further preferred that the MRI scanner is designed such that the middle axis (symmetry axis) of the toroidal main magnetic field B0 is positioned horizontally, i.e. the field lines of the toroidal main magnetic field lie on a vertical plane. It could also be said that the Y-axis of the main magnetic field (or the local y-axes of the imaging regions) is oriented horizontally.

It is further preferred that one side wall of the imaging region (formed by an outer housing of a magnet segment) is positioned in a horizontal plane. This has the advantage that a patient my lie on this side wall, e.g. on a patient bed arranged there. In an exemplary embodiment, a patient table is arranged horizontally and especially could be moved along a vertical direction and/or along a horizontal direction in order to shift and center the anatomical region of interest (ROI) within a patient body into and/or inside the imaging region.

There can be only one imaging region, such that a round MRI scanner may look like "PacMan", however, there could also be two imaging regions, preferably in a mirrored arrangement, especially such that there is a number of magnet segments between the imaging regions forming a wall between the imaging regions together with the housing of the MRI scanner. An MRI scanner with two mirrored imaging areas looking like the imaging areas of a "PacMan" MRI scanner could be designated as "mirrored PacMan" MRI scanner.

In order to generate the pulsed magnetic field gradients required for spatial signal encoding and to run the MR sequences, a preferred embodiment of an MRI scanner further uses a number of V-shaped planar gradient coils.

Such (toroidal) MRI scanner can especially be used for all applications described in the previous and the following paragraphs. It is particularly useful for applications for MR-guided radiation therapy and interventional radiology.

According to a preferred embodiment the MRI scanner with a number of V-shaped imaging regions is combined with a further medical imaging component and/or intervention component and/or a therapy component, especially an X-ray component. Preferred components are radiographic imaging devices, tomographic imaging devices and/or X-ray sources for radiotherapy (radiation therapy). However other non-X-ray devices are also preferred. A special advantage of a V-shaped imaging region is the space that is provided for easy interactions from the outside during an MRI procedure.

The "PacMan" arrangement or the respective mirrored arrangement (PacMan-like, but with two V-shaped imaging regions) is especially advantageous for treating a patient while lying on a patient bed. A star shaped or other arrangement with a toroidal field having a vertical axis is advantageous for a standing or sitting patient.

Preferred is an MRI system that is designed for the field of Magnetic Resonance guided Radio Therapy ("MRgRT", may also be designated as "Magnetic Resonance guided Radiation Therapy"), especially for on-line image guidance for application of different forms of local therapy, e.g. radiotherapy ("RT" or "radiation therapy") in form of image-guided radiotherapy ("IGRT", also "Image Guided Radiation Therapy"), highly focused ultrasound ("HIFU"), thermal ablation or respective methods. Such MRI system would be advantageous up to fundamental to precise application of a therapeutic dose, in order to achieve maximum effect on tumor tissue and at the same for minimizing the damage on healthy tissues surrounding that tumor.

Currently, the most frequently used method of 3D image verification is performed by using cone beam CT ("CBCT"). However, computer tomography ("CT") has limiting soft-tissue contrast which is essential for good delineation of tumor tissues. However, MR is prone to provide improved guidance to existing targets and the opportunities for guidance to new types of targets. MR is applicable to external beam radiation therapy ("EBRT") as well as for brachytherapy. The ultimate goal of MR-guided RT (MR-gRT) would be to exploit superior soft-tissue contrast provided by MRI and its ability to use imaging biomarkers.

Early shrinkage of tumor or lymph nodes can be such potential biomarkers that could potentially indicate a treatment response and, thereby, allowing to adaptively modify the treatment in an online fashion. Instead of just changing the treatment plan, due to anatomical changes without changing the original treatment intent (as most current adaptive RT techniques do), MRgRT when fully realized, will be able to change the treatment intent based upon the continuously acquired real-time data. It collects biomarkers and is able to use biomarkers to identify responders compared with non-responders. Thus, MRgRT with real-time adaptive plan optimization, especially when performed with the MRI system according to the disclosure, will be a game changer in radiation oncology.

In an exemplary embodiment, the MRI-system is designed for intensity-modulated radiation therapy ("IMRT"). This is an advanced mode of high-precision RT that uses computer-controlled linear accelerators ("LINACs") and/or other radiation sources (e.g. X-ray sources or γ-ray emitting radioactive isotopes) to deliver a precise beam of radiation to a malignant tumor. Thus, a preferred MRI system comprises a number of LINACs or other radiation sources (e.g. γ/X-ray sources), arranged such that its beam (their beams) can be led into at least one of the imaging regions. Especially it comprises two or more LINACs (and/or two or more other radiation sources, e.g. γ/X-ray sources) in the case of two or more imaging regions. In an exemplary embodiment, the control of the MRI system is designed such that images or other information taken by the MRI scanner can be used for controlling the number of LINACs and/or other radiation sources (e.g. γ/X-ray sources).

It is particularly preferred that the MRI system is designed for acquiring images and controlling the number of LINACS at the same time. Such that radiotherapy (radiation therapy) and MRI can be performed synchronously. Thus, influences of the beam of a LINAC, especially therapeutic effects of the LINAC beam, can be directly monitored by MRI.

IMRT allows for the radiation dose to conform more precisely to the 3D shape of a tumor. It achieves that by modulating the intensity of the radiation beam in multiple small volumes and multiple beam directions. IMRT also allows higher radiation doses to be focused on the tumor while minimizing the dose to surrounding normal critical structures. Because the ratio of normal tissue dose to tumor dose is reduced to a minimum with the IMRT approach, higher and more effective radiation doses can safely be delivered to tumors with fewer side effects compared with conventional techniques. IMRT also has the potential to reduce treatment toxicity, even when doses are not increased.

A conventional shuttle-based MRI-assisted radiotherapy (radiation therapy) system operates a mobile patient table in shuttle mode to transport the patient forth and back in-between a standard MRI scanner and an ancillary therapy system that is a LINAC gantry. It means that multiple imaging and the therapy session are interleaved in time but never performed simultaneously. Although regular MR images can be acquired this way to guide the therapy procedure, logistics associated with repeated patient and image registration make this a daunting exercise in most radiation therapy departments.

However, more recent developments have provided RT (radiation therapy) with the ability to have on-board MRI coupled to the RT unit. As said above, this tool for treating cancer is known as MR-guided RT (MRgRT). Several varieties of these units have been designed and installed in centers across the globe. However, in all those systems the patient table movement is either absent or very restricted, necessitating on-line re-planning and causing slow throughput. Patient access is limited during treatment and claustrophobic patients may be unable to have treatment. Special calibration equipment must be used that fits the tight magnet bore and is compatible with a magnetic field. Furthermore, those prior-art systems have limitations regarding the beam area and the beam angulation that can be scanned and thereby restrict the advantages of IMRT procedures. This reduced the freedom to develop a high-quality treatment plan in some cases, e.g., head-and-neck tumors and stereotactic body radiotherapy (radiation therapy). Moreover, all the existing MR-LINAC systems above are incompatible with traditional LINAC gantries and therefor need specifically designed LINACs. Clinical adoption of these systems has to absorb a high cost burden of the new system development and facility deployment. For those clinics that already have LINACs installed, purchasing a new and expensive MR-LINAC is a particular concern.

The preferred MRI system discloses a new open MRI scanner solution (due to the V-shape of an imaging region) using a toroid magnet, especially the so-called "PacMan" MRI scanner (or the respective mirrored arrangement) described above, and its applications in the field or MRgRT.

A major advantage of this magnet solution is that there is only a weak stray magnetic field outside the scanner volume, even when the magnet is not actively shielded. This is especially important for hybrid systems like MRI scanners for radiotherapy (radiation therapy) or interventional rooms, since parts of equipment like the LINAC or alternatively the gamma photons sources and a multi-leaf collimator have to be placed in regions with only weak stray magnetic field. Thus, due to the reduced stray magnetic field, the motion of these components will not significantly disturb the magnetic field within the MR imaging region.

According to a preferred method, such MRI scanner with a horizontal orientation of the Y-axis of the main magnetic field is used for MRgRT applications. In an exemplary embodiment, real-time images of tumor tissues are acquired and used to correct the angulation of a collimated therapy beam, especially by controlling a radiation source (preferably a LINAC therapy source, another radiation (e.g. γ/X-ray) therapy source and/or a (multi-leaf) collimator) based on these MR images acquired parallel to the therapy (i.e. at the same time).

Unlike prior art solutions, there are many degrees of freedom in positioning the radiation beam relative to the patient body and to the target area. In an exemplary embodiment, a radiation source, e.g. a γ/X-ray source, is arranged in a distance bigger than half the radius of the MRI scanner from the patient bed (or the center axis of the main magnet arrangement). Suitable positions for the radiation (e.g. γ/X-ray) source are the wall of an imaging region (the therapy room), the outer enclosure of the MR-scanner or a mounting structure outside the imaging region.

In an exemplary embodiment, the MRI system comprises a patient table, having at least one or preferably multiple degrees of freedom in motion, e.g. vertically, horizontally and/or rotating around a vertical axis.

In an exemplary embodiment, the MRI system comprises a radiation source that is designed to be moved to various positions and respective angulations. The radiation source can especially move along a 90° path by rotating around a longitudinal patient axis and/or (further) along a 180° path by rotation around the X-axis of the system (the MRI scanner). Generally, these paths could be adapted to the necessary movement. Preferred angular movements are along an angel>20°, preferably along an angel>40° or even along an angel>60°, but preferably less or equal 180° or 90° respectively. This allows for much better freedom in modulating the applied radiation dose and thereby providing better patient outcome when using IMRT methods for elaborating a high-quality treatment plan in challenging clinical cases e.g. head-and-neck tumors and stereotactic body radiotherapy (radiation therapy).

For movement, the radiation source (especially a LINAC and a multi-leaf collimator) are preferably positioned on a rotating arm that is able to rotate around a system axis of the MRI scanner to change an angulation between the therapy beam and a patient body.

A special advantage of this disclosure is that the new MRI scanner is compatible and can be directly used with existing and with traditional LINACs. Clinical adoption of these systems does not need to absorb a high cost burden of the new system development and facility deployment. For those clinics that already have LINAC gantries installed, it will be only required to purchase the new MRI scanner and install it.

Furthermore, it is preferred to combine a (especially mirrored) PacMan MRI scanner or a MRI scanner with multiple imaging regions with other types of existing RT equipment that uses a robotic arm to position the therapy beam at many various positions around the patient. Although LINAC systems are mentioned as examples for existing equipment for reference implementations, the MRI adaptation described herein is not limited to LINAC systems and can be adapted to other radiotherapy (radiation therapy) machines, for example a low-energy Co-60 therapy machine e.g. a therapy machine using radioactive Co-60 isotopes emitting Trays.

In numerous medical diagnostic and interventional applications, it is desirable to use both, MR image data and image data obtained from X-ray based imaging systems. In certain procedures, it would be useful to provide additional feedback to medical personnel of the state of tissues and anatomies based upon a combination of imaging modalities. For example, during catheterization, angioplasty, and similar procedures, MRI systems may permit a surgeon to identify soft tissues through which a probe is inserted, but are not necessarily well suited to imaging tissues indicative of the actual location of the probe.

Because surgical interventions happen in real time, currently available technologies for separate modality imaging are not suited to providing this type of information and feedback. Furthermore, interventional and therapy procedures, like for example the ones involved with the invasive treatment of liver tumors and metastasis, will benefit from availability of registered real-time multiple-contrast medical images.

It is well known in the art that X-ray images are efficiently supplemented by MR images because MR images provide a good soft-tissue contrast whilst the X-ray imaging is an efficient way of depicting bone structures and injected contrast media.

Combinations of imaging modalities for interventional radiology are known in the art as Angiographic Magnetic Resonance hybrids, or AMR systems for short. An integrated AMR system that makes use of different imaging modalities in a complementary fashion provides the required feedback to surgeons and other medical professionals about the physical conditions of a subject, particularly during interventional procedures.

However, conventionally, MR imaging and X-ray imaging are performed at different times using an MRI scanner and an X-ray imaging equipment separate from the MRI scanner and to register together the two image sets providing different anatomy contrasts. In this case, however, the patient must be transported between the two different imaging units or even relocated. Furthermore, because of the time delay between the two procedures, it is possible that the anatomy of the patient can change, for example due to respiration or metabolic processes. This complicates the fusion of the MR images with the X-ray images. This shuttle-based MRI-assisted interventional system needs to transport the patient forth and back in-between a standard MRI scanner and an ancillary X-ray interventional or angiographic system. It means that multiple imaging and the interventional session are interleaved in time but never performed simultaneously.

Although regular MR images can be acquired this way to guide the interventional procedure, logistics associated with repeated patient and image registration make this a daunting exercise in most interventional radiology departments.

However, more recent developments have provided interventional X-ray systems with the ability to have on-board MRI. Several varieties of these units have been designed or installed in centers across the globe. In all these conventional systems the patient table movement is restricted to the longitudinal direction due to the shape of the bore of the solenoid MRI systems used. The access to the patient body for surgeons and for the medical personnel during treatment is much restricted. Moreover, claustrophobic patients may be unable to have treatment. Special calibration equipment for the X-ray components must fit the tight magnet bore and shall be compatible with a magnetic field. Furthermore, those prior-art systems have limitations regarding the beam area and the beam angulation that can be scanned and thereby restrict the advantages of 3D imaging procedures. This further reduce the freedom to develop a high-quality interventional or surgery plan in many cases. Moreover, the solutions above are incompatible with traditional X-ray equipment and therefore need specifically designed devices. Clinical adoption of these systems has to absorb a high cost burden of the new system development and facility deployment. For those clinics that already have X-ray imaging devices installed, purchasing a new and expensive AMR is a particular concern.

According to a preferred embodiment of the disclosure, an MRI system with a toroidal field and an "open" MRI scanner, especially a MRI scanner with a V-shaped imaging region, preferably the "PacMan" MRI scanner or a MRI scanner with multiple imaging regions (e.g. the "mirrored PacMan" scanner), is applied in the field or interventional radiology.

A major advantage of this magnet solution is that there is only a weak stray magnetic field outside the scanner volume even when the magnet is not actively shielded. This is especially important for hybrid systems like MRI scanners for interventional rooms, as other parts of equipment like the X-ray tube or the beam collimator will be placed in regions with only weak stray magnetic field and therewith their motion will not significantly disturb the magnetic field within the MR imaging region.

Preferred is an AMR hybrid scanner solution using such MRI system according to the disclosure (e.g. the "PacMan" MRI scanner) to generate real-time MR images and a number (e.g. one or two) of X-ray imaging units. Each unit e.g. comprising at least one X-ray source and at least one digital X-ray detector. The MR images show soft tissues that can be fused together with X-ray images collected by e.g. two digital X-ray detectors as a patient body is exposed to an X-ray beam emerging out of an X-ray tube. Thus, the MRI system is designed for a parallel acquisition of MR images and X-ray images (at the same time).

Unlike conventional solutions, there are many degrees of freedom in positioning the X-ray source relative to the patient body and to the target anatomy region due to the open structure of the imaging region. In an exemplary embodiment, an X-ray detector is arranged on, in or under a patient bed and an X-ray source is arranged in a distance bigger than half the radius of the MRI scanner from the X-ray detector. Suitable positions for the X-ray source are the walls of an imaging region (e.g. a surgery room), the outer enclosure of the MR-scanner or a mounting structure outside the imaging region.

Again, in an exemplary embodiment, the MRI system comprises a patient table, having at least one or multiple degrees of freedom in motion (e.g. vertically, horizontally and/or rotating around a vertical axis).

In an exemplary embodiment, the MRI system comprises an X-ray source (radiation source) that is designed to be moved to various positions and respective angulations. The X-ray source can preferably move along a 90° path by rotating around a longitudinal patient axis and/or (further) along a 180° path by rotation around the X-axis of the system (the MRI scanner). Generally, these paths could be adapted to the necessary movement. Preferred angular movements are along an angel>20°, preferably along an angel>40° or even along an angel>60°, but preferably less or equal 180° or 90° respectively. This allows for much better freedom in the generation of the 2D projection images recorded at the detectors and for elaborating of a high-quality treatment plan in challenging clinical cases by using e.g. stereotactic X-ray radiology.

For movement, in an exemplary embodiment, the X-ray source (radiation source) is positioned on a rotating arm that is able to rotate around a system axis of the MRI scanner to change the angulation between the therapy beam, e.g. an X-ray beam) and a patient body.

According to a preferred method, multiple X-ray projection images acquired at various angulations (view angles) are used by means of the method known as digital tomosynthesis to generate CT-like slice images through the patient body. Especially, these images are registered with MR images taken simultaneously to the X-ray projection images.

Digital tomosynthesis is a method for performing high-resolution limited-angle tomography at radiation dose levels comparable with projection radiography. Tomosynthesis image reconstruction delivers slice images by using algorithms similar to CT reconstruction. Due to partial data sampling (limited view angles) with very few projections, approximation algorithms have to be used. Filtered backprojection and iterative, expectation-maximization algorithms have both been used to reconstruct slice images. Reconstruction algorithms for tomosynthesis are different from those of conventional CT because the conventional filtered backprojection algorithm requires a complete set of data. Iterative algorithms based upon expectation maximization are most commonly used. Manufacturers of such systems use off-the-shelf GPUs to perform this reconstruction in a few seconds.

A special advantage of this disclosure is that the MRI scanner according to the disclosure (e.g. the "PacMan" MRI scanner) is compatible and can be directly used with already available and with traditional X-ray imaging systems. This is because of the open imaging regions. Clinical adoption of these systems does not need to absorb a high cost burden of the new system development and facility deployment. For those clinics that already have X-ray imaging systems installed it will be only required to purchase the new MRI scanner and install it.

According to a preferred embodiment, a (especially mirrored) "PacMan" MRI scanner hosts a patient table (patient bed) with an integrated X-ray detector and preferably multiple degrees of freedom in motion. The MRI system comprises X-ray equipment delivering an imaging beam toward an imaging region (a patient on the table), wherein multiple imaging regions can be delivered by multiple X-ray sources with suitable beams.

In an exemplary embodiment, the MRI system comprises an X-ray tube mounted on a telescopic arm, which is especially able to move along rails, e.g. mounted on the ceiling along an OX-axis and independently along an OY axis. The system is especially designed to rotate the X-ray tube to adjust the angulation between the X-ray beam and the imaging region (a patient).

Furthermore, it is preferred to combine a (especially mirrored) PacMan MRI scanner or a MRI scanner with multiple imaging regions with other types of existing X-ray equipment that uses a robotic arm to position an X-ray beam at many various positions around the patient. For example, if a breast cancer screen indicates an abnormality, a biopsy of the suspicious tissue will be taken for closer examination, which requires exquisite targeting of the suspicious tissue. A combination of MRI imaging and X-ray would locate the exact target. The robot then guides the biopsy needle holder with the lesion so that the doctor can insert a needle precisely.

Concerning the MR-scanner architecture according to the disclosure, that are targeted to scan multiple objects or patients in parallel at the same time in different imaging regions, there are different methods to actually perform these measurements. One preferred measurement is a parallel or simultaneous measurement of objects in the imaging regions.

As said above, a (parallel) MR-scanner that is based on a toroidal magnet, unlike the conventional MR magnets that use solenoid or Helmholtz-pair magnet coils, has the advantage that the toroid coils tend to confine the magnetic field inside the torus with only a small and not so far reaching stray magnetic field. In the following, a six-pack toroidal MR-scanner having six examination regions (imaging regions) and allowing for scanning up to six patients simultaneously is regarded as example. This solution provides six imaging regions wherein the homogeneity of the magnet field B0 is good enough for conducting data acquisition and image reconstruction also with methods well-known in the art of MRI.

It is preferred to assign a local (individual) coordinate system XYZ for each imaging region. The local Z-axis is running parallel to and pointing in the same direction with the static magnetic field B0. The Y-axis is parallel to the rotational symmetry axis of the six-pack magnet system (i.e. e.g. pointing up), while the X-axis corresponds to the radial direction pointing from the center of symmetry outwards from the magnet.

When such a MR-scanner according to the disclosure operates in parallel mode in order to scan many patients simultaneously, a problem results since the scan-related activities in one active region would interfere with the scan course within another adjacent (nearby located) imaging region. For example, the gradient coils activated to generate a magnetic field variation across one imaging region may also produce stray fields outside the target imaging region far away and deep into the adjacent regions. Such stray fields will perturb the signal encoding and the data acquisition within the adjacent imaging regions. The same effects would result for the RF transmit coil, which once activated to apply RF energy to the object within the target imaging region will also radiate a leak RF field penetrating the adjacent regions and thus interfering with the local scan processes, thereby possible leading to perceptible image artefacts.

Up to now, there are no suitable solutions known from the prior art that would be a first-hand fit for these new MR-scanner architectures according to the disclosure, providing multiple imaging regions for simultaneously imaging many subjects in parallel.

Surely, new gradient coils could be invented that are optimized for an MR-scanner having a toroidal magnetic field and particularly for MR-scanners with prismatic imaging regions. These gradient coils could allow special countermeasures to correct for the interference induced into adjacent imaging regions.

However, in order to deal with those interferences described above, the inventors have recognized that it will be of special advantage when the MR sequences (also called "pulse sequences") that run within the various imaging regions are either identical and synchronous or at least similar but still operating synchronously. In this way a hazard for the worst-case interfering conditions to occur is eliminated. The stray fields in adjacent regions could then be regarded and treated as belonging to the measurement itself.

In a gradient system for a magnetic resonance imaging system according to an exemplary embodiment of the disclosure, the gradient coils are arranged in at least two imaging regions. The system additionally comprises a gradient controller designed such that it controls the electric current flowing through at least two gradient coils for similar gradient axes in different imaging regions in a temporal synchronous manner.

A gradient system typically comprises gradient coils arranged in an imaging region, e.g. at the basic field magnets confining an imaging region. Although the coils may comprise many different loops of a wire, all wire-loops on one side of an imaging region that produce a gradient on the same axis are regarded as one single coil in the following.

The gradient controller may be a component providing control signals for a current for the gradient coils (e.g. as a controller for power amplifiers) as well as a unit providing the current itself (e.g. in the case the gradient controller comprises the respective power amplifier). The gradient controller is designed such that it controls the electric current flowing through at least two gradient coils in a temporal synchronous manner, i.e. at the same time. In an exemplary embodiment, a gradient controller is designed to coordinate all gradient activities, preferably the independent or synchronized operation of different gradient axes, especially even the minimization and/or the correction of cross-interference terms between the gradient coils.

Regarding gradient axes in different imaging regions, it should be noted that the gradient axes should follow local coordinate systems in the individual imaging regions. Typically, the z-gradient axis follows the basic magnetic field. In a toroidal arrangement, the z-axes (all together) will run in a circle or a polygon, since the orientation of the basic magnetic field is different in every imaging region and it has the shape of a circle or polygon. Similarly, the X-axis, typically pointing perpendicular to the basic magnetic field and parallel to the plane of the toroidal shape, will differ in every imaging region, always pointing to the outside in the plane of the toroidal basic magnetic field. The y-axis typically points perpendicular to the basic magnetic field and its toroidal plane. In an exemplary embodiment, for each imaging region there is a local coordinate system XYZ associated therewith, wherein the local Z-axis is running parallel to and pointing in the same direction with the static basic magnetic field B0, the Y-axis is parallel to the vertical rotational symmetry axis of the MRI-scanner, while the X-axis corresponds to the radial direction pointing from the center of symmetry outwards from the magnet through the vertical midplane of the imaging compartment.

Coils for similar gradient axes are both Z-gradient coils in the two imaging regions or both X-gradient coils or both Y-gradient coils. The axes do not have to point in similar directions, they have to be the same axes concerning the local coordinate systems of the gradient coils in the individual imaging regions.

A further global coordinate system may be connected to the whole MRI-scanner. This global coordinate system preferably includes a vertical Y-axis (the same as the rotational symmetry axis), a radial R-coordinate pointing from the symmetry axis radially outwards and an angular Θ-coordinate. For a star shaped arrangement of the basic field magnets of a MRT-scanner, the spatial relations between the global and the local coordinate systems are as follows: the local Y-coordinates are always equal to the global Y-coordinate. A local X-axis corresponds to a radial spoke going through the vertical midplane of an imaging compartment. All the local Z-axes together combine to build up the sides of a polygon cutting through the horizontal midplane of the magnet and centered around the symmetry axis.

Surely, the gradient system should also comprise further components that the gradient systems of the state of the art also comprise for an optimal operation. These are e.g. dedicated gradient power amplifiers for each axis GPAx, GPAy and GPAz, shim coils or holding structures.

Such gradient system has the advantage that it produces a special, synchronized gradient field. It is very advantageous for MRI-scanners with inclined arrangements of basic field magnets as e.g. star-shaped arrangements. It is also advantageous for above mentioned "satellite scanners".

A preferred method, especially to control such gradient system, to apply a gradient field for at least two imaging regions with gradient coils, comprises the step:
  applying an electric current flowing through at least two gradient coils for similar gradient axes in different imaging regions in a temporal synchronous manner.

Thus, there are at least two gradient fields applied in two different imaging regions on similar axes (either X or Y or Z axis) at the same time. Surely, the method can be applied to more than one axis, so that two axes or all three axes are driven synchronically, wherein the synchronous operation is essential for any similar axes.

A magnetic resonance imaging system according to a preferred embodiment of the disclosure comprises a basic field magnetic arrangement (i.e. a main magnetic field generation unit) for generating a main magnetic field and multiple spatially separated imaging volumes (measurement stations). The MR imaging system is configured to utilize the main magnetic field generated by the basic field magnetic arrangement commonly for the multiple imaging volumes, wherein the MR imaging system is configured in a way that at least two imaging volumes of the multiple imaging volumes at least two patients can be scanned simultaneously. Furthermore, the MR imaging system is configured to employ an imaging protocol which is adapted to the simultaneous scanning of the at least two patients at the at least two imaging volumes in order to reduce a required time for the simultaneous scanning and/or in order to reduce interferences between the simultaneous measurements (scanning) at the at least two imaging volumes.

Figure 23:
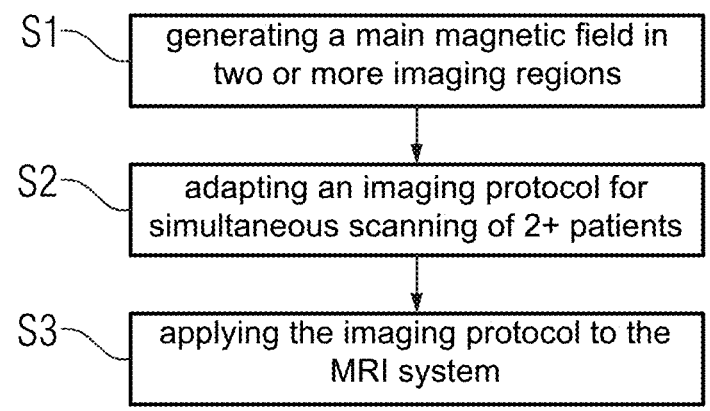
FIG. 23 is a flowchart of a method for controlling a MRI system according to an exemplary embodiment.

As illustrated in FIG. 23, a method for controlling a MRI system according to an exemplary embodiment of the disclosure comprises:
  Generate a main magnetic field in two or more imaging regions, i.e. multiple spatially separated imaging volumes (Step S1). This main magnetic field could be generated by the basic field magnetic arrangement as described above.

Utilize the generated main magnetic field commonly for the multiple imaging volumes, wherein in at least two imaging regions (of the multiple imaging volumes) at least two patients can be scanned simultaneously, i.e. one patient in one imaging region and not two or more patients in one single imaging region.

Optionally: Generate preferably global magnetic field gradients operating synchronously in all and over all the imaging regions.

Employ an imaging protocol which is adapted for the simultaneous scanning of the at least two patients at the at least two imaging regions (measurement stations) in order to reduce a required time for the simultaneous scanning and/or in order to reduce interferences between the simultaneous measurements (scans) at the at least two imaging volumes (Step S2).

Apply the imaging protocol to (or with) the magnetic resonance imaging system (Step S3).

This system and method has the advantage that additional corrections and algorithmic methods intended and applied to reduce or eliminate these interferences would be much simpler to elaborate and to implement. All steps concerning the method can also be applied as features of the system by components that are designed to perform the corresponding method steps.

Thus, this preferred embodiment reveals a new operation mode for the parallel MRI scanner that will not impose additional restrictions for the clinical workflow. It means that there will be no additional wait time or dead-time for the parallel imaging regions, even when all regions run the same sequences in a synchronous mode (what is a preferred embodiment).

In the following, a preferred imaging protocol is described that allows a measurement where every patient will be able to enter the imaging region at any convenient time and exit the imaging region after completion of the imaging protocol.

Preferred is a method of controlling an MRI system, especially for a scanning patients having the same clinical indication e.g. for breast cancer screening or needing a follow-up examination for prostate disease. This method comprises the step of applying an imaging protocol comprising or consisting of a succession of (a few) separate scans. In an exemplary embodiment, these scans are conducted by using an MR imaging sequence with predefined imaging parameters that provides the specific image contrast. A preferred prostate follow-up protocol comprises a number of scans from the group T1-weighted scans, T2-weighted scans, diffusion-weighted imaging scans, contrast agent-free perfusion imaging scans and spectroscopic MRI scans, e.g. it consists of a T1-weighted scan, followed by a T2-weighted scan, followed by a diffusion-weighted imaging scan, a contrast agent-free perfusion imaging scan and finally a spectroscopic MRI scan.

An MR sequence is a temporal succession of RF-pulses and gradient pulses that repeats during the scan with various gradient amplitudes until all data needed to reconstruct an image has been acquired. To acquire data, conventional MR sequences can be used. Alternatively, even new, dedicated and optimized MR sequences could be developed. It is preferred that every scan consists of multiple, e.g. 128, repetitions of the same sequence and the associated signal measurements. It is further preferred to measure as long as there can be acquired a data matrix known in the art as the k-space, e.g. with 128×128 data samples. In an exemplary embodiment, multiple data samples, usually 128, that fill-in a full line into the k-space matrix are measured for each repetition of the MR sequence. It is preferred to set the amplitude of the phase encoding gradient pulses Gy for each repetition in order to select the next k-space line to be acquired.

A preferred embodiment of the method, comprises the application of identical or at least similar sequences that are running synchronously with patients having the opportunity of (or actually are) being scanned asynchronously. That means that in all imaging regions similar or identical MR sequences are applied parallel (at the same time), e.g. regarding a parallel MRI scanner having six imaging regions. In this case, all six imaging regions are operated synchronously, e.g. by measuring a diffusion-weighted contrast. This operation mode is especially advantageous for scanning many patients for the same clinical indication or for screening numerous patients for a certain disease.

In an exemplary embodiment, the method is designed such that an MRI scanner comprising multiple imaging regions (i.e. being able to simultaneously scan up several patients), cyclically runs a temporal succession of the same examination protocol synchronously in every imaging region in a measurement cycle. There may be multiple measurement cycles, however, it is preferred that every measurement cycle is performed synchronously in every imaging region of the MR-scanner. This means that it is preferred that in every cycle and in each imaging region the scanner control system applies the same time succession of RF pulses and gradient pulses. In this way the risk of electromagnetic interferences between various imaging regions is minimized.

This preferred method also relies on the fact that it is, generally, not important in which time-succession the k-space matrix is filled-up. Important is only that enough samples are available to be introduced into this matrix allowing to reconstruct a full image. Thus, it is preferred that the time of one patient entrance into a first imaging region is independent from the time of another patient entrance into a second imaging region. Thus, doors to imaging regions are preferably controlled independently by the preferred method.

Thus, in a method according to an exemplary embodiment, a patient can entry or exit an (examination) imaging region at any point in time. There will be no deadlock or waiting time that would suspend the clinical workflow. A single technician or nurse would be able to assist every patient, to prepare the patient for the MR examination and to discharge the patient after the examination have been completed.

According to a further preferred method, a patient may entry the imaging region even in the middle of a running scan. In the case, a patient enters an imaging region at a point in time, when the scanner is already running through a scan. Thus, only a part of the k-space matrix of this scan will be acquired for the patient, and accordingly, the patient should complete the first run of the (complete) protocol and remain inside the scanner also during the second (following) run of this protocol until the corresponding point in a scan where the examination actually started. By this way the k-space data matrix for all scans of the protocol will be fully completed.

Especially, a point of time when a patient enters an imaging region and his/her examination starts during a running imaging protocol is monitored relative to this imaging protocol. The examination of the patient is then ended when the according point of time in the following imaging protocol is reached or exceeded (as said above, there are many measurement cycles where always the same imaging protocol is applied successively). Thus, according to a preferred method, when an examination on a patient is started during a running imaging protocol the point of time relative to this protocol is monitored when the examination started and the examination of the patient is ended (and the patient can leave) when the according point of time in the following (identical) imaging protocol has been reached.

This preferred method is also flexible enough to allow larger time gaps in between scanning two patients just in case one specific patient will require a longer preparation time. This may be the case for elderly patients with limited mobility, children or other special clinical cases.

A preferred embodiment of the method, comprises the application of similar or identical sequences that are running synchronously with a group of patients having the opportunity of being (or actually is) scanned synchronously and/or simultaneously. That means that in all imaging regions similar or identical MR sequences are applied parallel (at the same time), e.g. regarding a parallel MRI scanner having six imaging regions, all six imaging regions are operated synchronously/simultaneously. This operation mode is especially advantageous for scanning a group of patients for the same clinical indication or for screening numerous patients for a certain disease at the same time.

There is a clinical workflow advantage for investigating a group of patients simultaneously with a pause between two protocol runs, allowing for changing the group of patients. This offers for example the opportunity for a nurse to prepare the whole group of patients together for the pending MR examination and to psychologically motivate the patients to keep together as a team and to complete the MR examination up to the end. This embodiment would provide a cheap solution for the problem many patients (predominately small children) have with MRI scanning by abandoning the scan before completion due to claustrophobic and/or anxious stress.

However, this pause is not always necessary, since the k-space may also be filled by identical protocols running in successive cycles. Thus, also a mixture of synchronous and asynchronous examinations is possible, where a group of patients is examined in a part of the imaging regions synchronously and other patients enter and leave other imaging regions of the same MR scanner asynchronously.

One further advantage provided by a synchronous operation of a parallel MRI scanner is that the acoustic noise generated in each imaging region is the same. Therefore, noise counteracting methods like e.g. active noise cancellation, noise beautification and the likes are much simpler to implement. Furthermore, the resulted noise acts less disturbing for the patients.

The disclosure advantageously discloses means to scan multiple patients simultaneously and, thereby, it facilitates democratization of MRI by avoiding long waiting lists for patients. Moreover, the particular scanner embodiments reduce the magnetic field fringes and thereby the clinical footprint necessary for installation and thereto associated costs. It also enables mobile or transportable MRI scanners, also an advantage for the democratization of MRI.

FIG. 1 shows a schematic representation of a magnetic resonance imaging system 1 ("MRI-system"). The MRI system 1 includes the actual magnetic resonance scanner 2 with an examination space 3 or patient tunnel in which a patient or test person is positioned on a driven bed 8, supporting the examination object O.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central controller 13 that is used to control the MRI system 1. In an exemplary embodiment, the controller 13 includes processor circuitry that is configured to perform one or more functions and/or operations of the controller 13, including controlling the MRI system 1.

In an exemplary embodiment, the central controller 13 includes a sequence controller 14 for measurement sequence control. With this sequence controller 14, the series of radio-frequency pulses (RF pulses) and gradient pulses can be controlled depending on a selected pulse sequence.

To output the individual RF pulses of a pulse sequence, the central controller 13 has a radio-frequency transmitter 15 that generates and amplifies the RF pulses and feeds them into the RF transmission antenna system 5 via a suitable interface (not shown in detail). To control the gradient coils of the gradient system 6, the controller 13 has a gradient system interface 16. The sequence controller 14 communicates in a suitable manner with the radio-frequency transmitter 15 and the gradient system interface 16 to emit the pulse sequence.

Moreover, the controller 13 has a radio-frequency receiver 17 (likewise communicating with the sequence controller 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstruction unit (reconstructor) 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central controller 13 can take place via a terminal 11 with an input unit 10 and a display unit 9, via which the entire MRI system 1 can thus also be operated by an operator. MR images can also be displayed at the display unit 9, and measurements can be planned and started by means of the input unit (possibly in combination with the display unit 9), and in particular suitable control protocols can be selected (and possibly modified) with suitable series of pulse sequence PS as explained above.

The manner by which suitable raw data are acquired by radiation of RF pulses and the generation of gradient fields, and MR images are reconstructed from the raw data, is known to those skilled in the art and thus need not be explained in detail herein.

Figure 2:
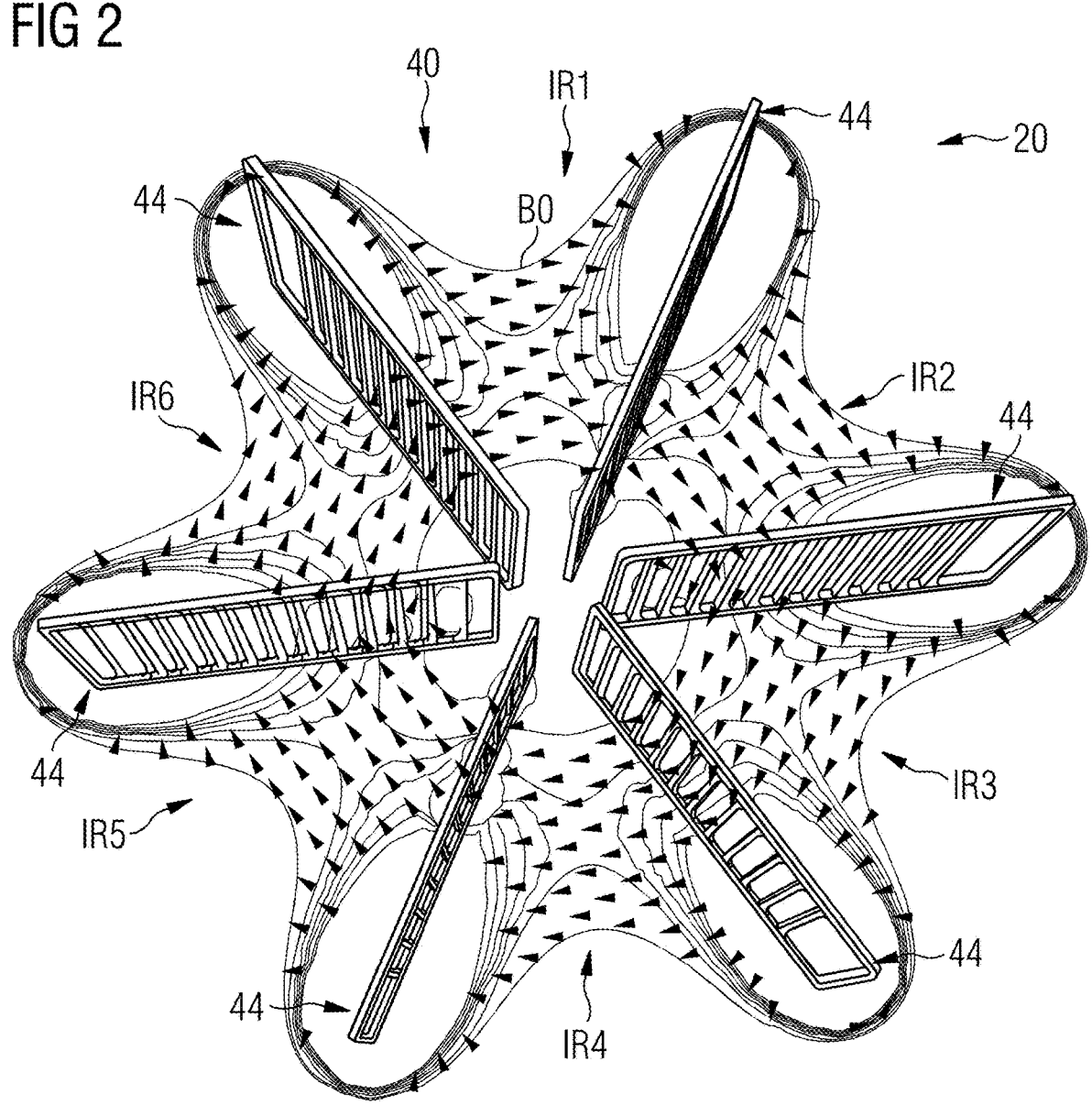
FIG. 2 shows the basic field magnetic arrangement of a toroidal MRI system according to an exemplary embodiment.

FIG. 2 shows the basic field magnetic arrangement 40 of a preferred toroidal MRI system 1, being the basis for a new MRI scanner 20. The basic field magnetic arrangement 40 comprises a main magnetic field system with at least one spatially separated segment (basic field magnet segments 44), which each generate a respective main magnetic field. The respective main magnetic fields of the multiple magnet segments are linked in an angular fashion to each other, so that the whole main magnetic field B0 has the form of a "toroid". The magnet segments 44 can be arranged in a star-shaped fashion. The idea is to insert the organ to be imaged (e.g. heart, jaw, breast) in the imaging region IR1, IR2, IR3, IR4, IR5, IR6 which is defined at least one cavity of the MR-scanner 20 of the toroidal MR system 1.

The system can be designed such that the toroidal magnet provides multiple imaging region s IR1, IR2, IR3, IR4, IR5, IR6 for simultaneous operation. Applications of such parallel scanning can be screening examinations, possibly even in the waiting area of a practice or hospital, or other mass patient scanning purposes.

The "six-pack" toroidal MR-scanner 20 could e.g. be used for dental imaging with six imaging regions IR1, IR2, IR3, IR4, IR5, IR6. The magnetic field distribution could e.g. lie between 0.1 T up to 3 T, especially between 0.8 T up to 1 T. In this image a global coordinate system OXYZ is shown that does not have to be the same with the local coordinate system of the imaging region IR1, IR2, IR3, IR4, IR5, IR6 (see also FIG. 19).

However, the system can also only provide a single, especially V-shaped, imaging region IR1.

Figure 3:
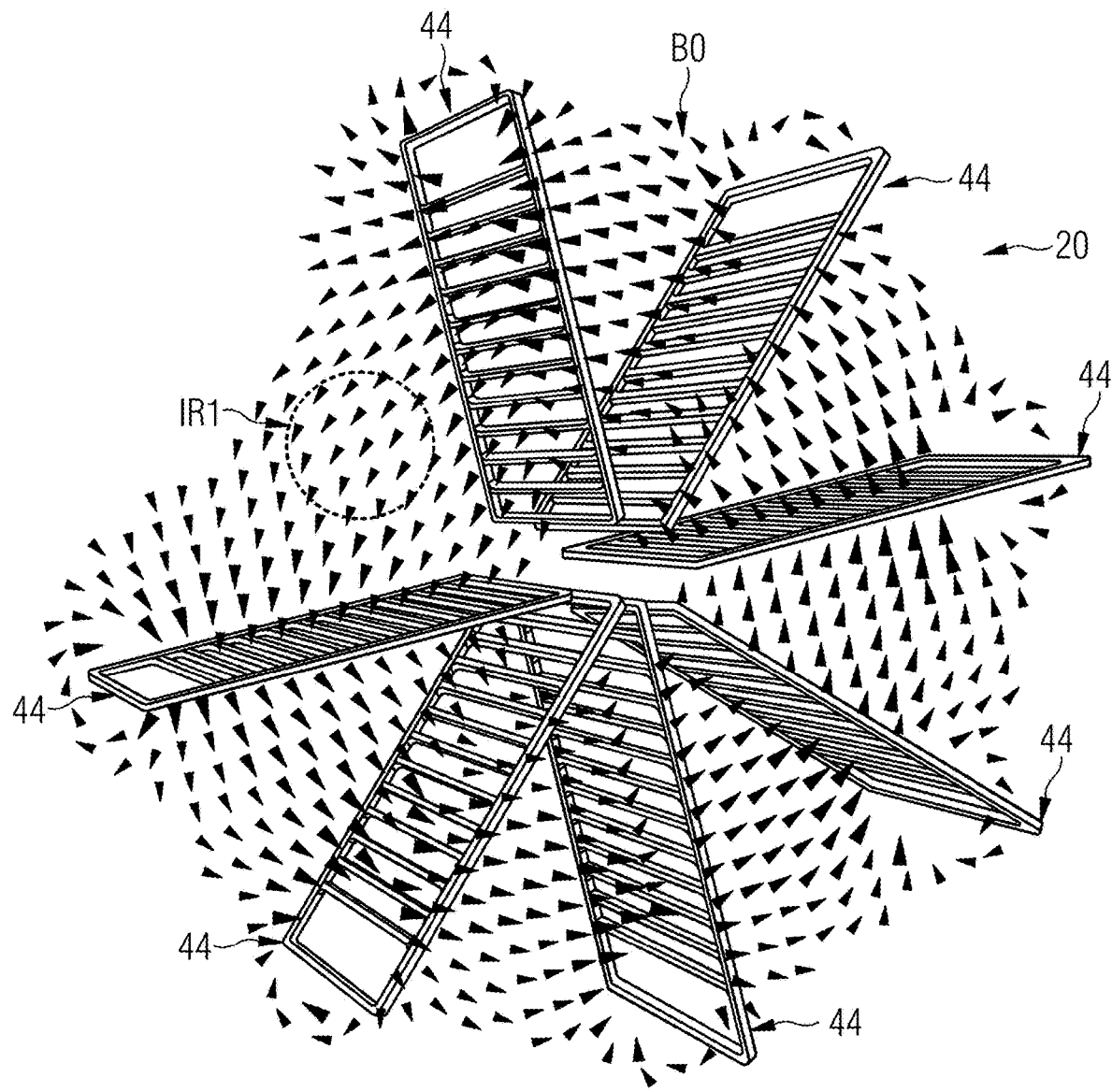
FIG. 3 shows a MRI scanner with a toroidal basic magnetic field and one single imaging region according to an exemplary embodiment.

FIG. 3 shows a MRI scanner 20 with a toroidal basic magnetic field B0 and one single imaging region IR1, i.e. only one cavity is provided to position the organ to be imaged in. The angular coverage of such imaging region IR1 can e.g. be between 45° and 90° degrees, in particular between 60° and 90° degrees. The setup is similar to FIG. 3 with a slightly different positioning of the basic field magnet segments 44 leaving only one V-shaped imaging region IR1.

The system can be adapted for different body organs, which may include the readjustment of shim irons of the magnet. The extension of the magnet and field generating coils along the symmetry axis can be set according to the target application. For example, a dental scanner will have an axial extension along the symmetry axis of preferably 20 cm, or in-between 15 cm and 30 cm. For prostate scanner the extension could be in-between 15 cm and 30 cm. For cardiac imaging the scanner extension can be in-between 30 cm and 60 cm.

The toroidal magnet used by the MR-scanner 20 could e.g. be used for dental imaging of a single patient. The circle shows the diameter of the (effective) imaging region IR1.

Figure 4:
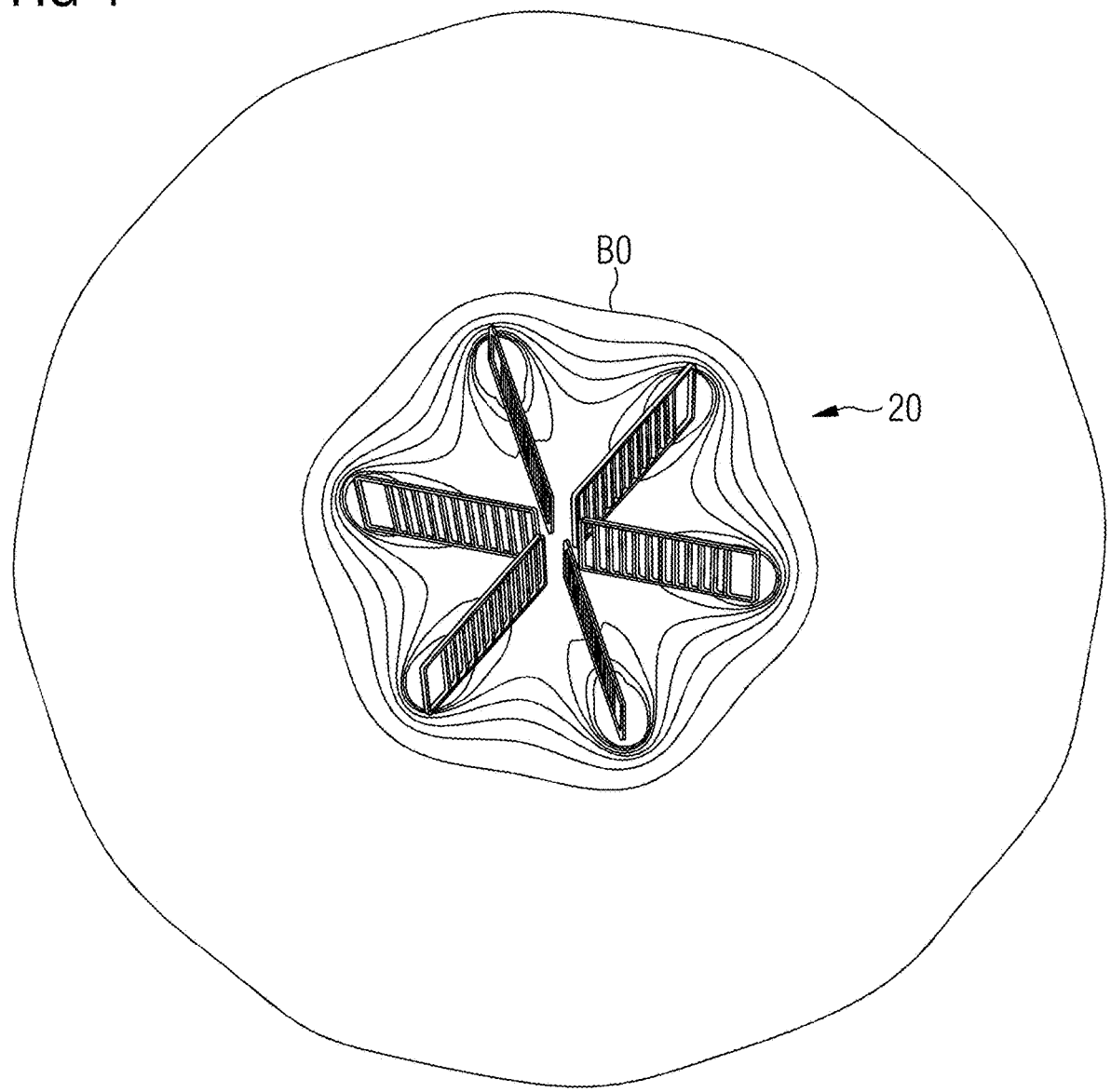
FIG. 4 shows the 5 Gauss outer contour for a 3 T dental MR-scanner with a toroidal magnet according to an exemplary embodiment.

FIG. 4 shows the 5 Gauss outer contour for a 3 T dental MR-scanner 20 with a toroidal magnet. The dimensions are shown in arbitrary units (a.u.) relative to the scanner size (=4 a.u.). This 5 Gauss contour has a radius of (further) 4 a.u. This radius will shrink proportionally even further when the static magnetic field intensity B0 is reduced from 3 T down to 1.5 T or down to e.g. 0.5 T. It can be seen that by using toroidal magnet systems for dedicated practitioner MRI scanners, such magnet configurations minimize the stray field and eliminate the need for active shielding coils, which makes these magnets also even more efficient and cost effective. This allows compact siting of the MRI scanners, even possible directly in the doctor's office without having to install them in a separate examination room.

Figure 5:
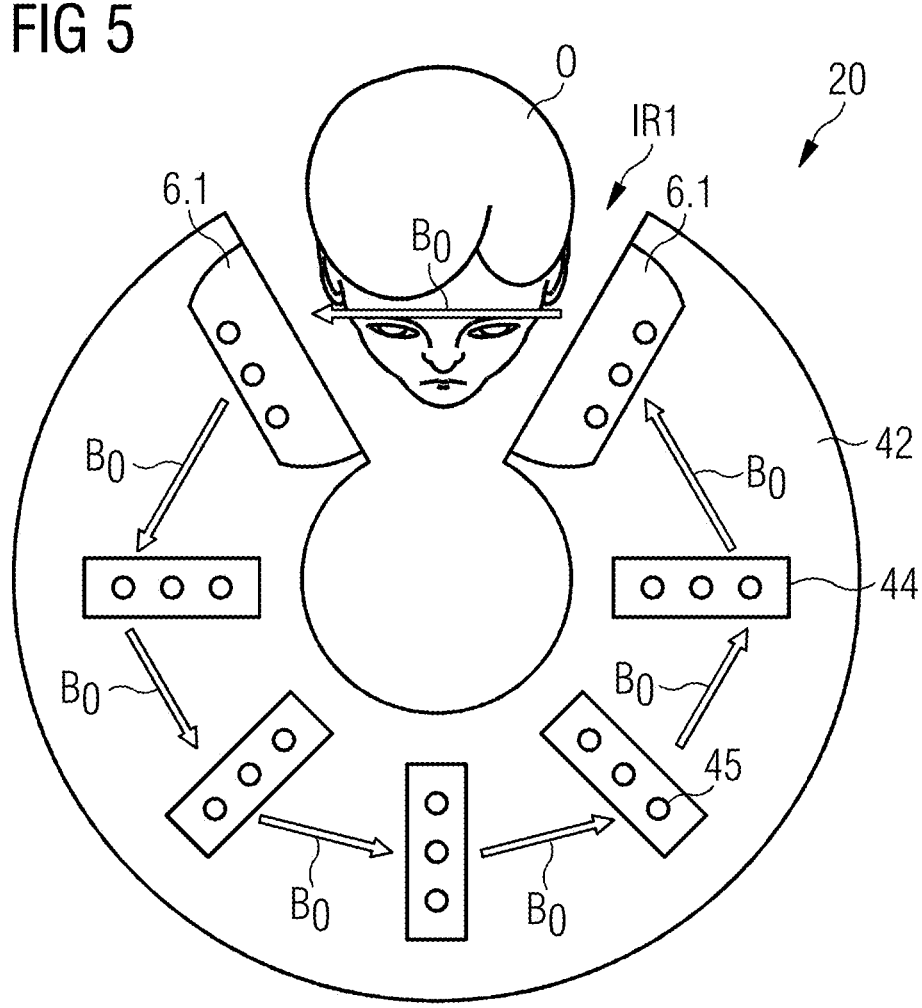
FIG. 5 shows a toroidal MRI scanner for dental imaging according to an exemplary embodiment.

FIG. 5 shows a toroidal MRI scanner 20 for dental imaging. The field strength could e.g. be assumed to be 0.1 T to 3 T. The jaw of the patient O is positioned with one of the cavities (or the single cavity, i.e. the imaging region IR1) of the toroidal magnet of the dental MRI scanner 20.

The patient O can stand during imaging or can furthermore lie on the back (e.g. on the treatment chair of a dentist). The toroidal MRI system (the MRI scanner 20) can be moved towards the patient O from the front, e.g. using a hinge mechanism which is fixed to the ceiling of the treatment room. Of course, the reversed configuration is also possible, i.e. the patient can lie on the back of his head in the cavity of the MRI scanner 20. The magnet (the coil arrangement 42) has multiple field generating coils (basic field magnet segments 44, only one marked) with coils having a planar distribution of wires 45 optimized such that the generated magnetic field B0 has parallel lines and it is homogenous enough at least for the imaging region contain the patient dental organ. The gradient coils 6.1 and/or the RF coils are preferably built into the magnet enclosure.

Figure 6:
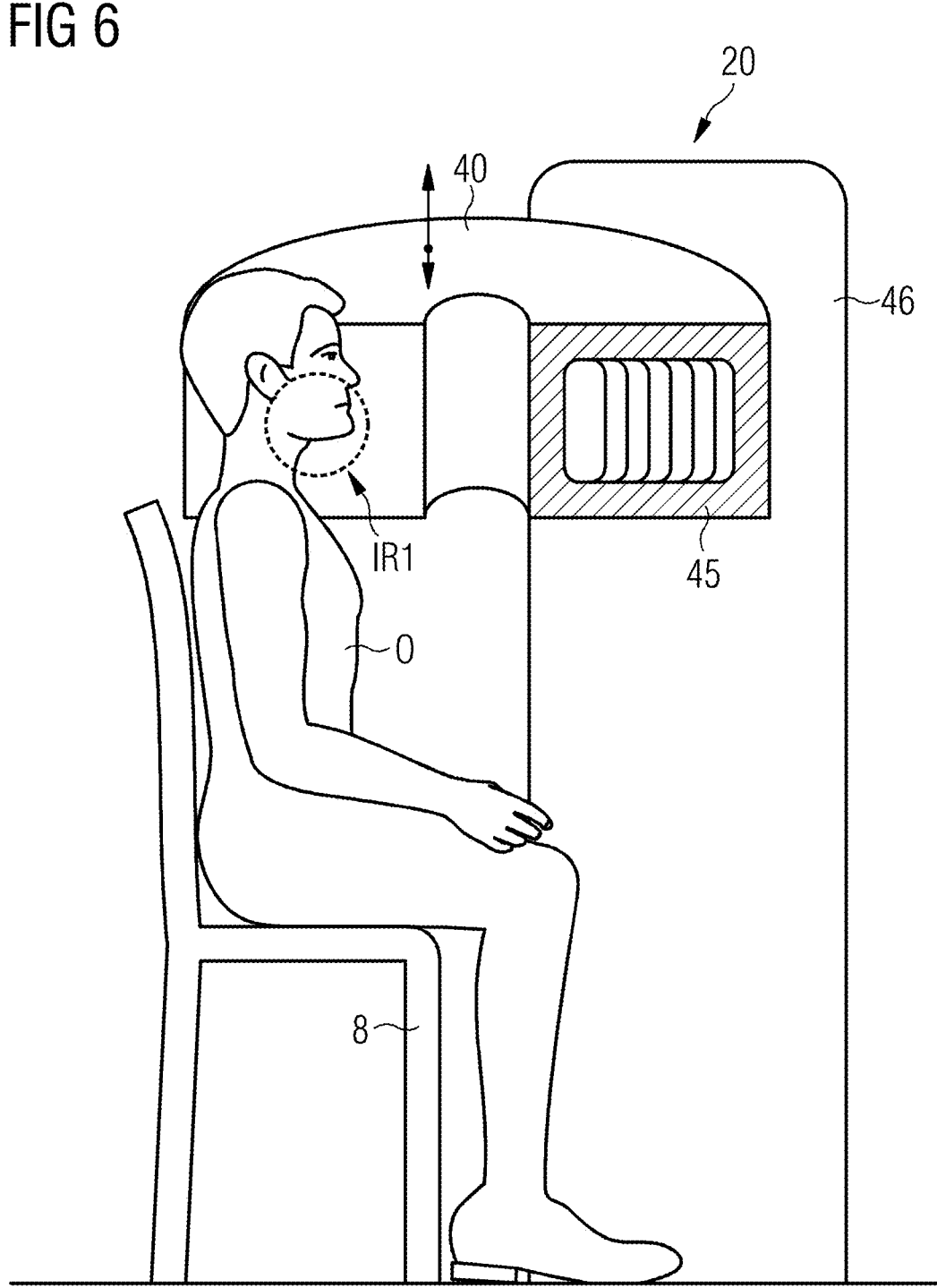
FIG. 6 shows a possible patient pose during dental MRI according to an exemplary embodiment.

FIG. 6 shows a possible patient pose during dental MRI. The patient O is sitting onto a patient chair 8 with the dental arches (the maxilla, or the mandibula or both) positioned within the magnet field-of-view FOV (the imaging region IR1). Either the patient chair 8 will be elevated or the main magnet (basic field magnetic arrangement 40) could be shifted along a post or along a vertical gantry 46. Additional positioning means such a conventional mouth fixture of panoramic X-ray dental imaging could be used to minimize or avoid motion during scanning.

In the basic field magnetic arrangement 40, also wire patterns 45 are shown that are used by the field generating coils. To increase patient comfort, the patient O can wear stereo goggles during imaging. Alternatively, small openings can be installed in the body of the MRI scanner 20 so that the patient O can see through those openings.

Figure 7:
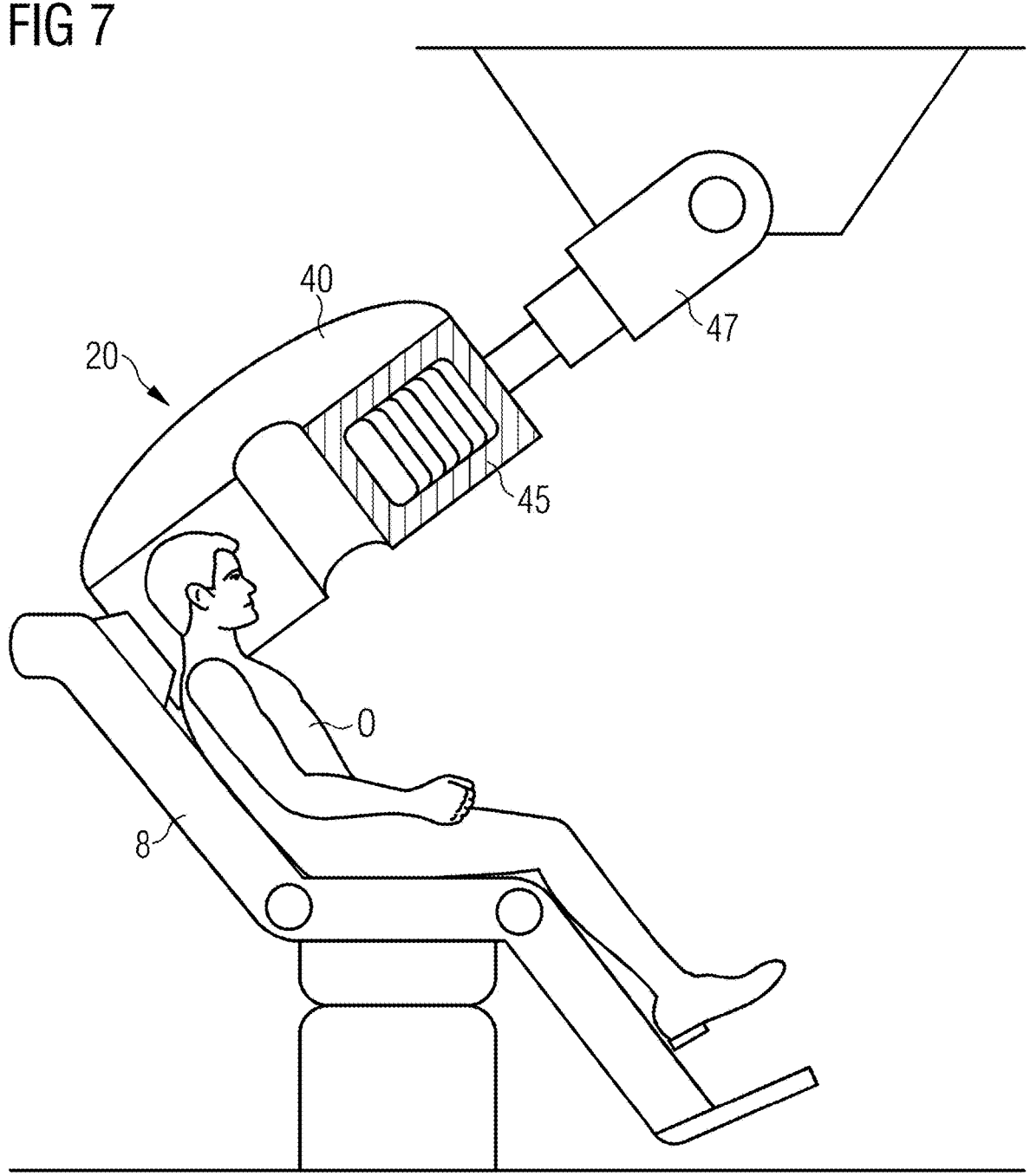
FIG. 7 shows another possible patient pose in a dental chair as for dental MRI according to an exemplary embodiment.

FIG. 7 shows another possible patient pose in a dental chair as for dental MRI, similar to FIG. 6 with the difference that instead of a gantry 46 the basic field magnetic arrangement is held and moved by a mechanical arm 47.

Figure 8:
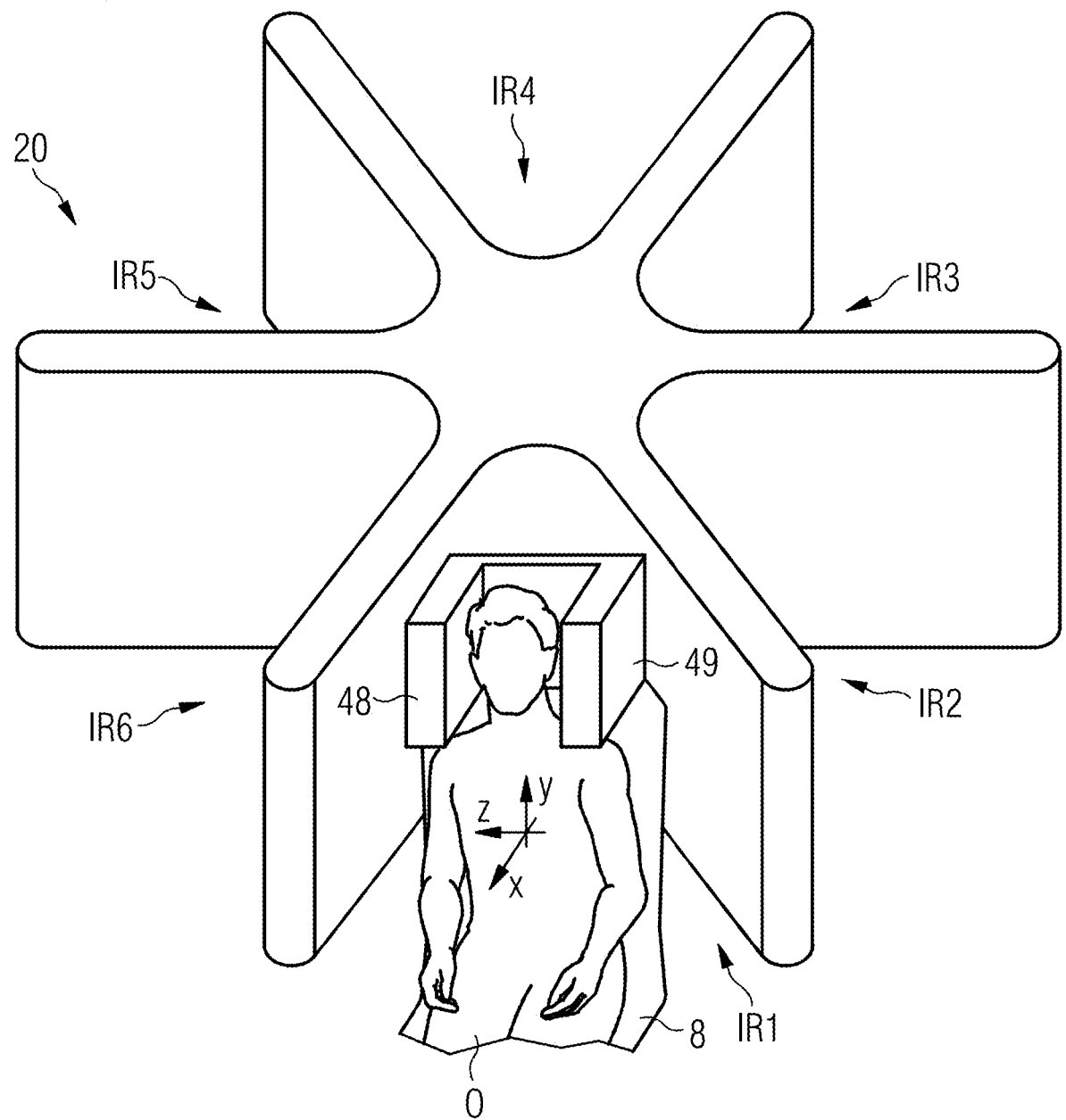
FIG. 8 shows one possible patient pose during head MRI according to an exemplary embodiment.

FIG. 8 shows one possible patient pose during head MRI. The patient O is sitting on a chair 8, the headrest (48, 49) attached to the patient chair 8 could host a local gradient coil, and/or a local shim coil and/or as well as the RF head-coils. The field strength of the main magnetic field should e.g. be 0.1 T to 3 T.

For cardiac or abdominal imaging, the patient thorax is positioned within one of the cavities (or the cavity) of the MRI scanner 20. The patient chair 8 will be elevated such that to position the organ of interest within the magnet FOV in the respective imaging slots (imaging regions IR1, IR2, IR3, IR4, IR5, IR6). For spine imaging, the patient O may sit on a chair 8 or stand while leaning upright and against a backrest with the backrest closest to the symmetry axis of the magnet. For prostate imaging the patient position could be the same as that depicted in this figure. Special prostate coils may be integrated into the patient chair 8. The field strength of the main magnetic field should preferably be 0.5 T for cardiac and 1.5 T or 3 T for prostate examinations.

For interventional breast imaging, a scanner configuration as depicted by FIGS. 6 to 8 is preferred. For mammography screening applications a configuration as that depicted by FIG. 8 will better fit the clinical needs of scanning as many as possible patients in given time. Alternatively, the patient pose within the imaging slot (imaging region IR1, IR2, IR3, IR4, IR5, IR6) could be such that the female patient O is sitting on chair while facing the vertical symmetry axis of the MR-scanner 20. The patient O could also stand while facing one separation wall of the imaging slot, which is with the shoulders line parallel to the local X-axis.

Figure 9:
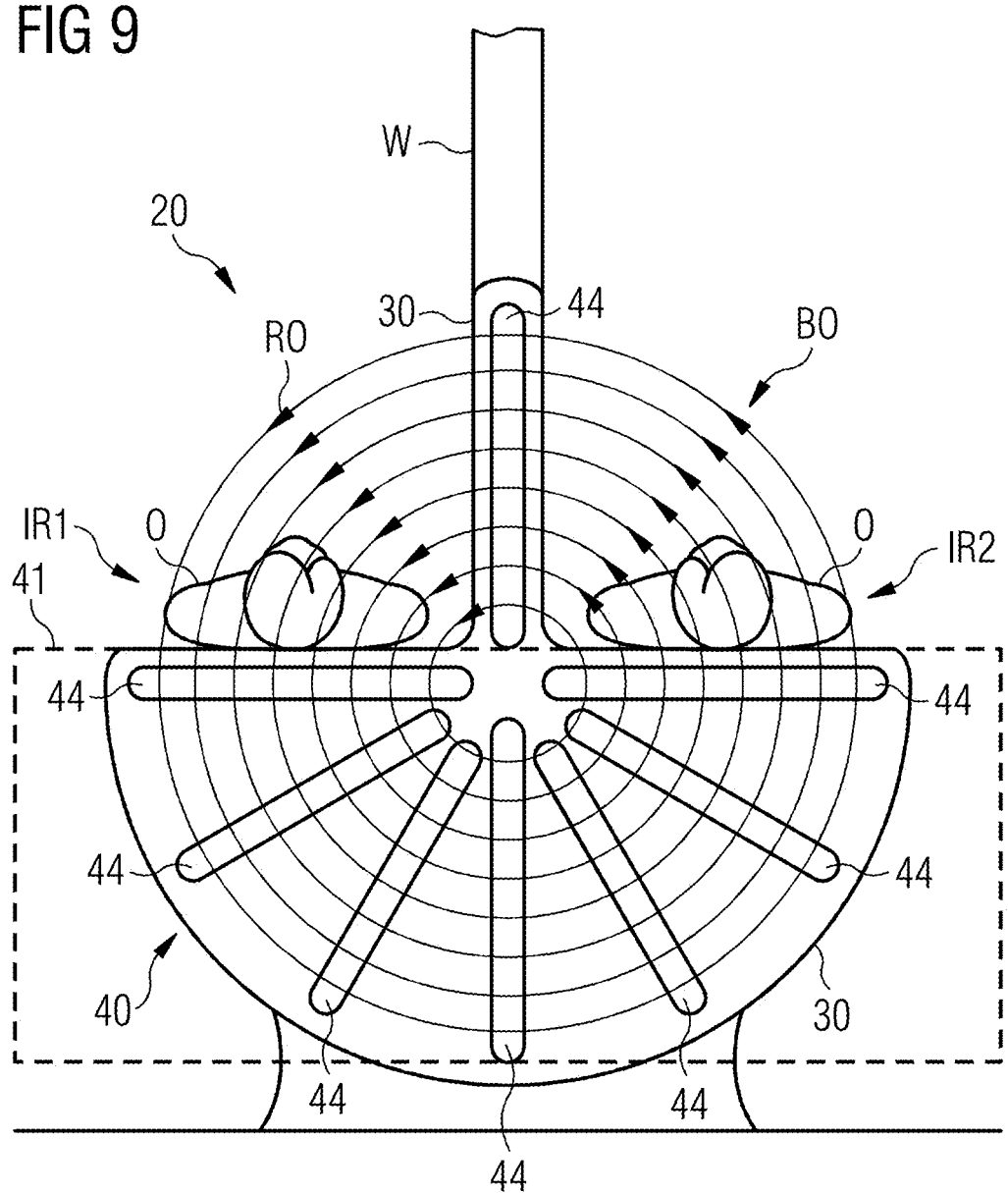
FIG. 9 shows an exemplary embodiment of a magnetic resonance scanner with two imaging regions.

FIG. 9 shows a further exemplary embodiment of a magnetic resonance scanner 2 with two imaging regions IR1, IR2 (that could be designated as "mirrored PacMan" MRI scanner 20. It is twin toroidal MR-scanner 20, especially advantageous for interventional MRI, e.g. for interventional prostate MRI.

Here, only the lower half of the basic field magnet arrangement 40 is designed star-shaped as a group 41 of basic field magnet segments 44 and another basic field magnet segment 44 projects upwards and serves both for guiding the basic magnetic field B0 as well as part of a wall W between two imaging regions IR1, IR2, on which there are two patients as objects O to be examined. In the illustration it can be seen that the lower part of the wall W between the two patients is formed by the housing wall 30 of the magnetic resonance scanner 20, into which the basic field magnetic segment 44 is integrated between the imaging regions IR1, IR2. The wall W can serve not only as a privacy screen but also as an acoustic shield or RF shield.

The basic magnetic field B0 of this magnetic resonance scanner 20 becomes weaker toward the outside, which can be used for location coding, and is homogeneous in the longitudinal direction (orthogonal to the image plane). It is basically the same in shape in the two imaging regions IR1, IR2, with the only difference being that the course (in one direction through the surface on which the patient O is lying) is reversed. Again, the dimensions of the magnetic resonance scanner 20 can be chosen quite different.

The basic magnetic main field direction R0 is also circular here. A special feature of this embodiment is that patients O are not in a narrow space, but can look freely to the ceiling. The inhomogeneity in the basic magnetic field B0, which is usually caused by the curvature, can be used, as mentioned, for spatial encoding resolution in one spatial direction.

Due to its open design and the toroidal magnetic field, this arrangement allows easy and little restricted access to the patient. As a result of the symmetric construction, magnetic forces are largely compensated or diverted into areas which can be reinforced structurally well.

Figure 10:
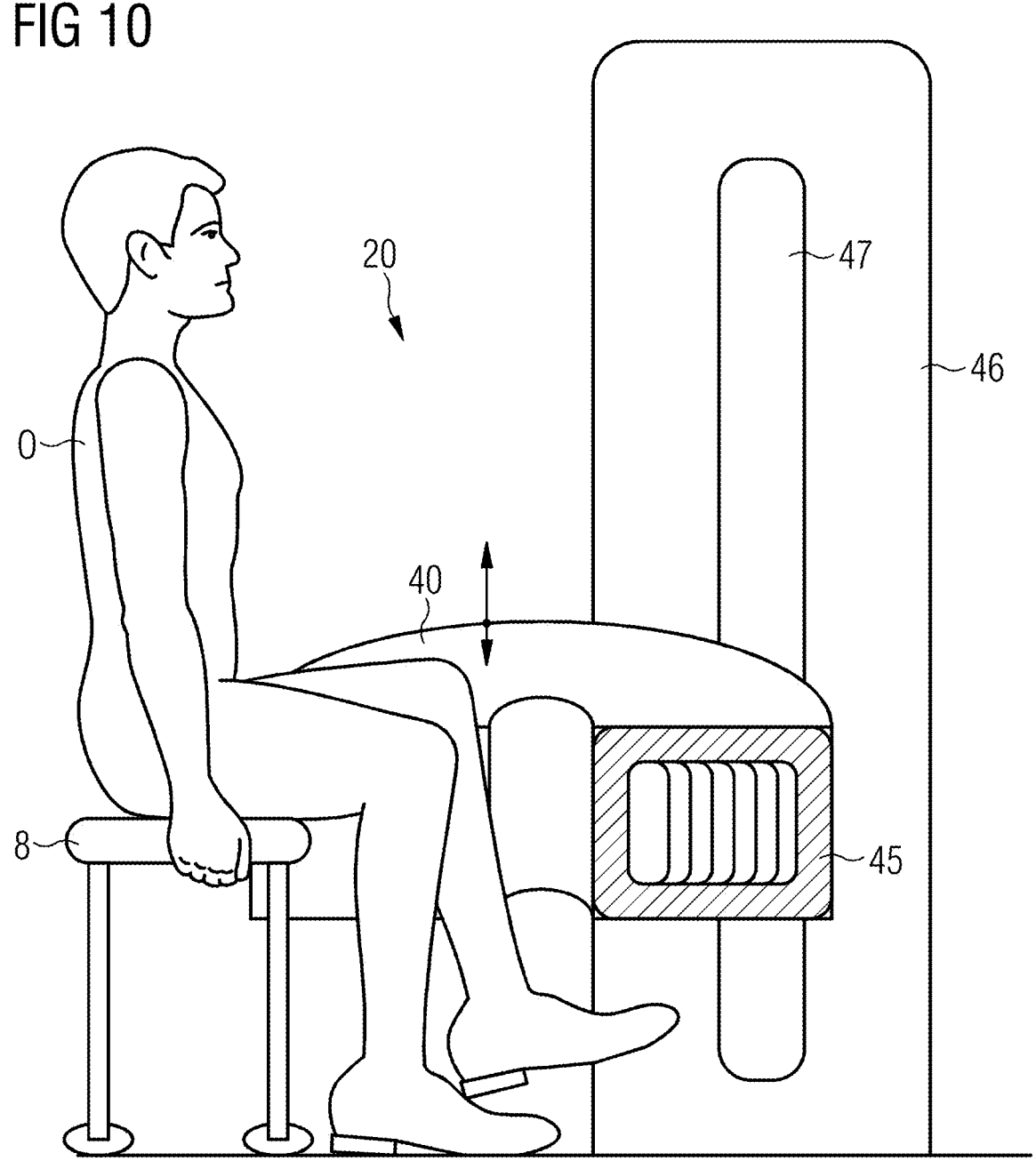
FIG. 10 shows one possible patient pose during MSK (knee) MRI according to an exemplary embodiment.

FIG. 10 shows one possible patient pose during MSK (knee) MRI. It is similar to the setups shown in FIG. 7 or 8 with a patient O sitting on a chair 8 and a basic field magnetic arrangement 40 held by a moving mechanism (e.g. an arm 47) in a gantry 46. The open configuration of the MRI system (the MR-scanner 20) makes kinematic examinations of joints of the patient O, i.e. imaging the joint of the patient O in motion, possible. Therefore, the patient O can sit or stand during examination, depending on which imaging setup for the patient's joint is desired.

The inventive solution facilitates a new open MRI scanner solution using a toroid magnet. This scanner solution is shown in the following and designated "PacMan" MR-scanner due to the similarity with the protagonist of the Pac-Man arcade game developed and released by Namco in 1980.

Figure 11:
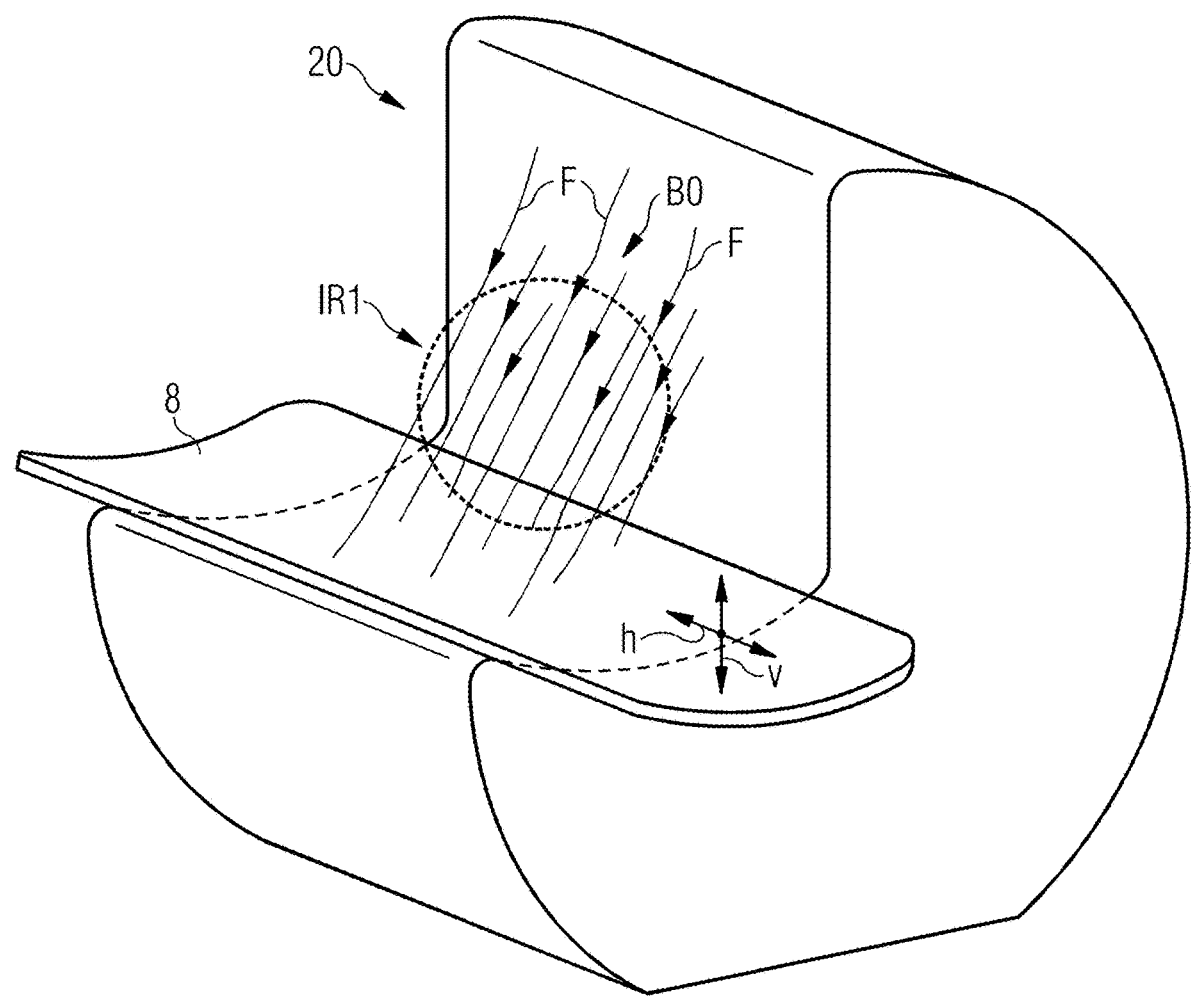
FIG. 11 shows a "PacMan" MR-scanner according to an exemplary embodiment.

FIG. 11 shows a "PacMan" MR-scanner 20 comprising a V-shaped imaging region IR1 having a spherical field-of-view FOV (the imaging region IR1) that is confining a static magnetic field B0 having parallel field lines F emerging out of the magnet faces. A patient table 8 could be moved along a vertical direction v and/or along a horizontal direction h, in order to shift and center the anatomical region of interest (ROI) within the patient body into the imaging region IR1.

Figure 12:
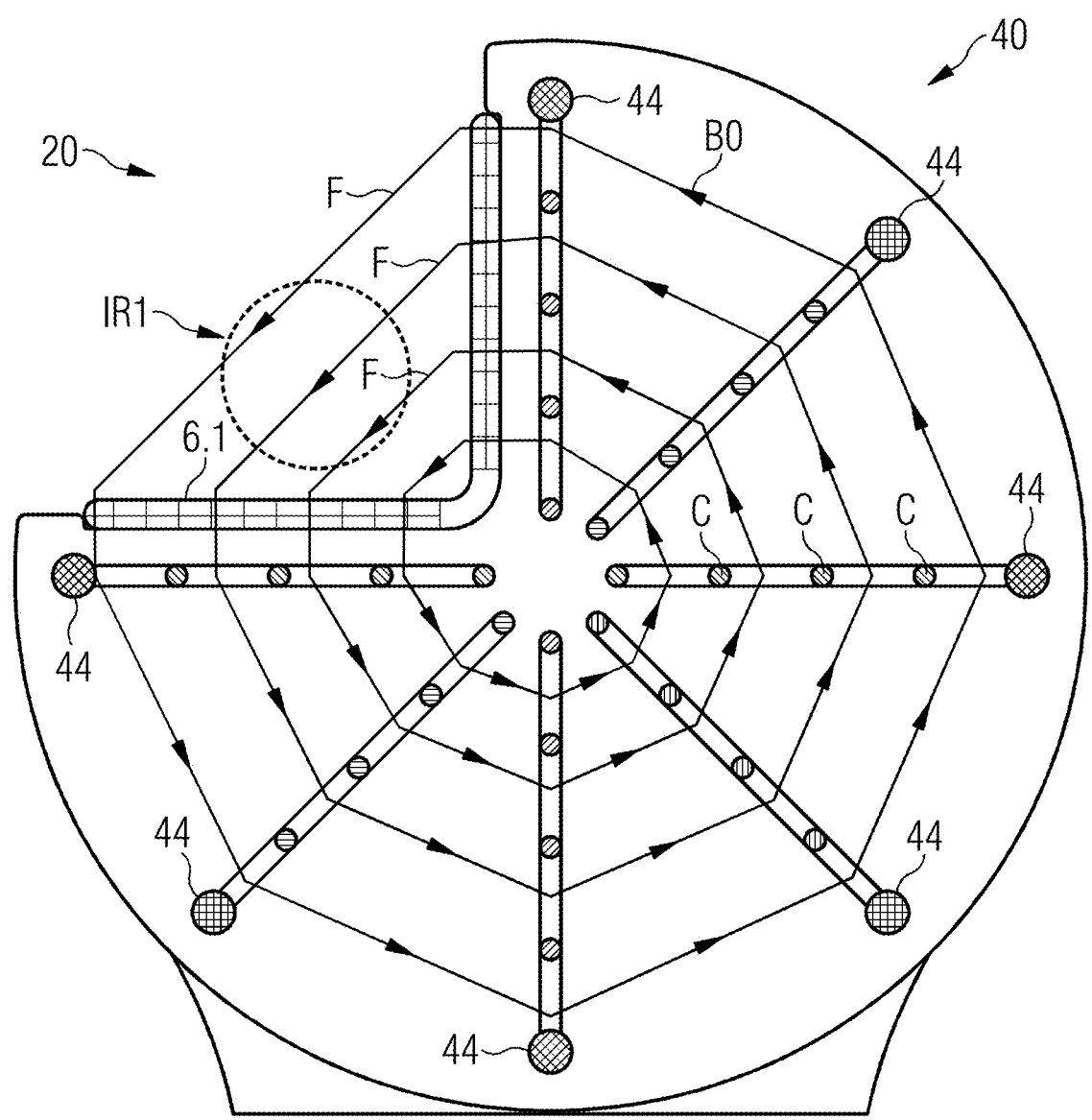
FIG. 12 shows a "PacMan" magnet according to an exemplary embodiment.

FIG. 12 shows a "Pac Man" magnet that can be used in a MR-scanner 20 as shown in FIG. 11 to generate the above disclosed static magnetic field B0. It comprises the basic field magnetic arrangement 40, wherein the toroidal magnet could be an electromagnet for low-field MRI (0.01 to 0.2 T) or a superconducting magnet for high-field MRI (0.1 to 3 T). The spherical homogeneity volume (being the imaging region IR1 in the MRI scanner 20) is part of the toroidal magnetic field having parallel field lines F at least within the imaging region IR1.

This toroidal magnetic field results by the current following into the field generating coils 44 (basic field magnet segments 44). The planar field generating coils need to provide a radially linear distribution of coils currents C in order to generate a toroidal static magnetic field having homogenous intensity along all closed field lines (i.e. the polygonal contours in this Figure). In an alternative embodiment, the static magnetic field B0 does not necessarily have parallel magnetic field lines F.

By controlling the radial distribution of wires/coil currents C across the planar magnet coils 44, it is possible to generate other field topologies, for example a magnetic field having circular field lines F.

In order to generate the pulsed magnetic field gradients required for spatial signal encoding and to run the MR sequences, this new scanner further uses a V-shaped planar gradient coil 6.1.

A major advantage of this magnet solution is that there is only a weak stray magnetic field outside the scanner volume (the volume of the MR-scanner 20), even when the magnet is not actively shielded.

Figure 13:
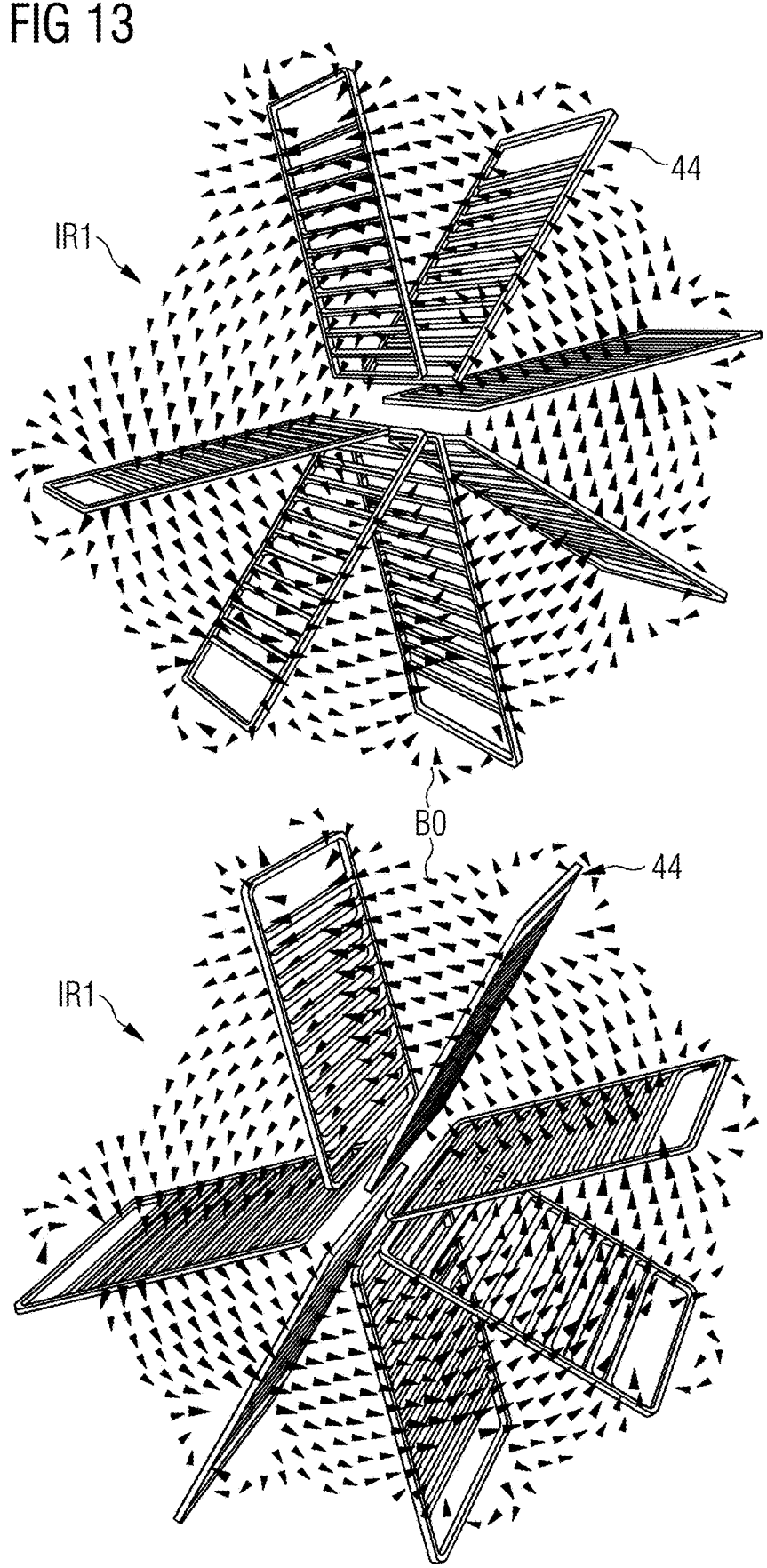
FIG. 13 shows a "PacMan" MR-scanner magnetic field configuration according to an exemplary embodiment.

FIG. 13 shows a "Pac Man" MR-scanner 20 magnetic field configuration of a field generated in a magnet arrangement as shown in FIG. 12 from two different angles of view. The minimum of the shown field strength is 0.5 T, the maximum is 1.5 T.

The PacMan toroidal MRI scanner can be used for all applications described in the previous and the following paragraphs. It is particularly useful for applications for MR-guided radiotherapy (radiation therapy) and interventional radiology.

Figure 14:
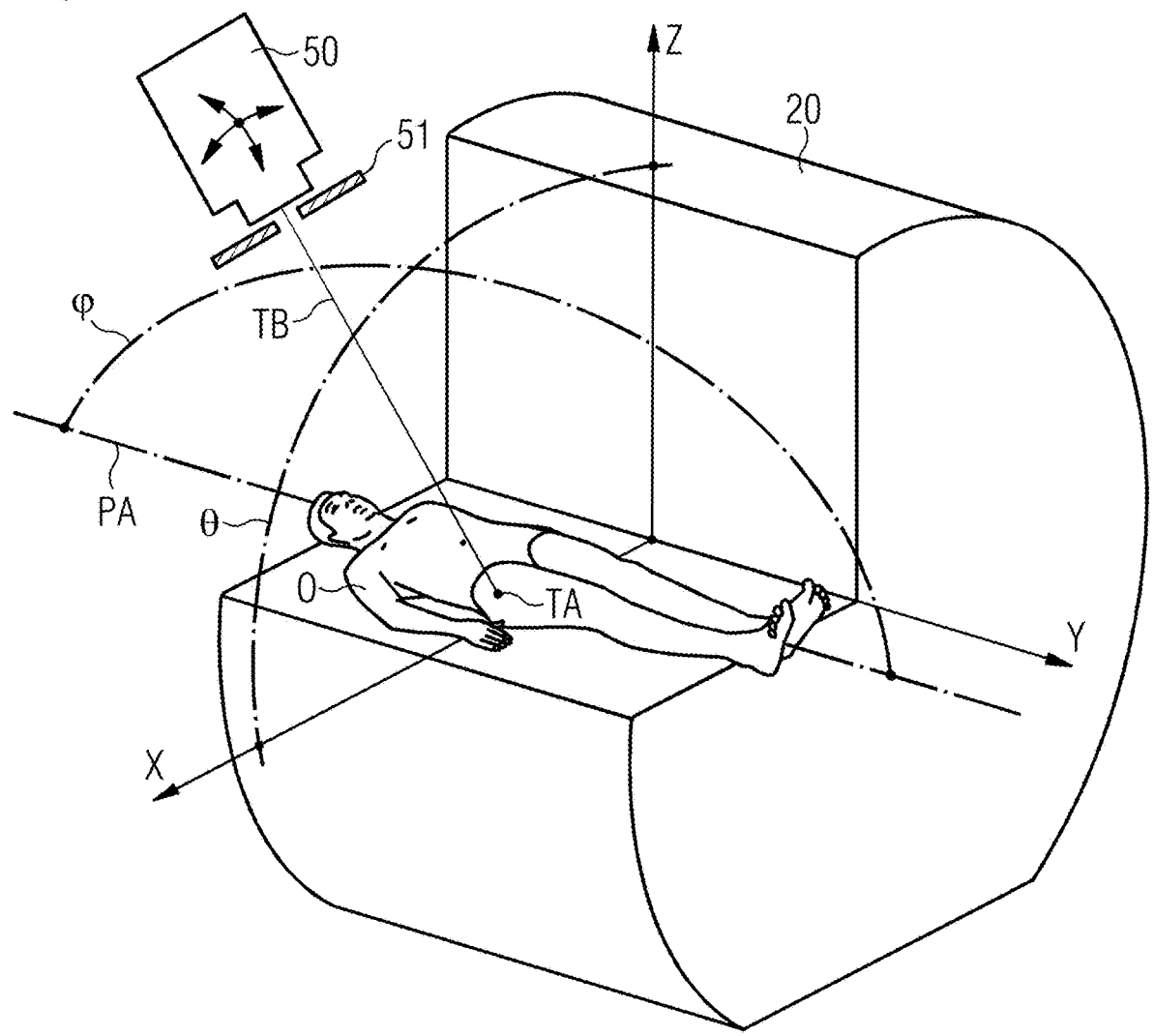
FIG. 14 shows an image guided radiotherapy (radiation therapy) system using a "PacMan" MR-scanner according to an exemplary embodiment.

FIG. 14 shows an image guided radiotherapy (radiation therapy) system using a "Pac Man" MR-scanner 20. The new MR-scanner solution is here used for MR-guided radiotherapy (MRgRT) applications. The above described "PacMan" MR-scanner 20 (see e.g. FIGS. 11 and 12) is used to generate real-time images of tumor tissues that are used to correct the angulation of a collimated therapy beam TB generated by a LINAC 50 therapy source (LINAC: linear accelerator) and collimated by a multi-leaf collimator 51.

The patient lies on a patient table 8 (not shown in this figure but similar to the one shown in FIG. 11). The patient table 8 has at least one or preferably multiple degrees of freedom in motion (e.g. vertically, horizontally and/or rotating around a vertical axis). Moreover, the radiation source 50 also can be moved at various positions and respective angulations. The radiation source can move along a 90° θ-path by rotating around a longitudinal patient axis PA and further along a 180° φ-path by rotation around the X-axis of the system. This allows for much better freedom in modulating the applied radiation dose and thereby providing better patient outcome when using Intensity-modulated radiation therapy (IMRT) methods for elaborating a high-quality treatment plan in challenging clinical cases, e.g. head-and-neck tumors and stereotactic body radiotherapy (radiation therapy).

Figure 15:
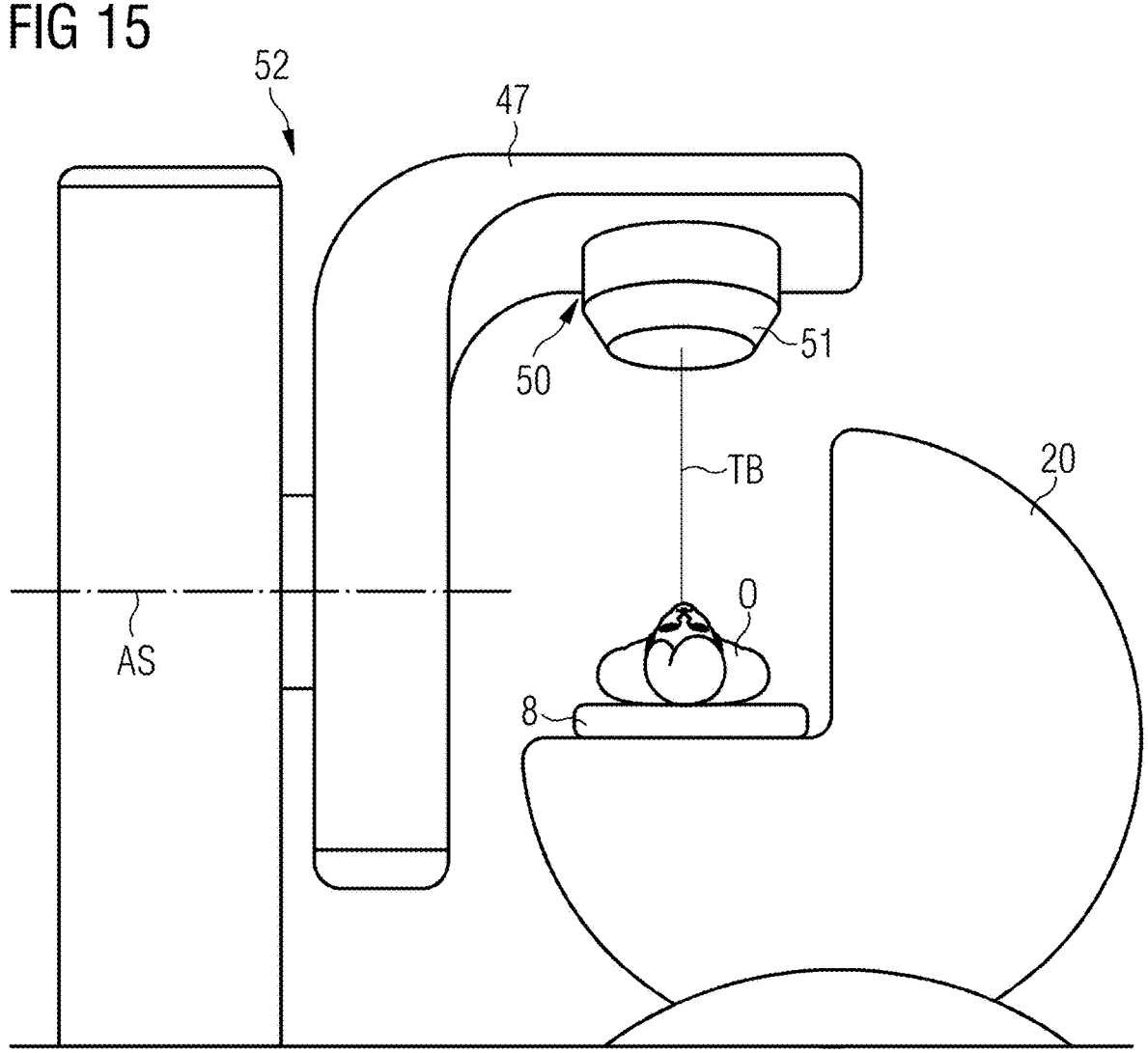
FIG. 15 shows an image guided radiotherapy (radiation therapy) system using a "PacMan" MR-scanner and an existing (available) LINAC gantry RT system according to an exemplary embodiment.

FIG. 15 shows an image guided radiotherapy (radiation therapy) system using a "Pac Man" MR-scanner 20 and an available LINAC gantry RT system. The new "PacMan" MR-scanner 20 is compatible and can be directly used with available and with traditional LINACs 50. Clinical adoption of these systems does not need to absorb a high cost burden of the new system development and facility deployment.

The PacMan MR-scanner 20 provides a patient table 8 with preferably multiple degrees of freedom in motion. The LINAC equipment 52 delivers the therapy beam TB to treat the patient O on table. The LINAC 50 and the multi-leaf collimator 51 are positioned on a rotating arm 47 that rotates around a system axis AS to change the angulation between the therapy beam TB and the patient body. It should be noted that all these functions are already available with existing LINAC equipment 52.

Furthermore, the PacMan MR-scanner 20 could be combined with other types of available RT equipment that uses a robotic arm 47 to position the therapy beam TB at many various positions around the patient O. Although LINAC systems 52 are shown as available equipment for reference implementations, the MRI adaptation described herein is not limited to LINAC systems 52 and can be adapted to other radiotherapy (radiation therapy) machines for example a therapy machine using a Co-60 radiation source.

Figure 16:
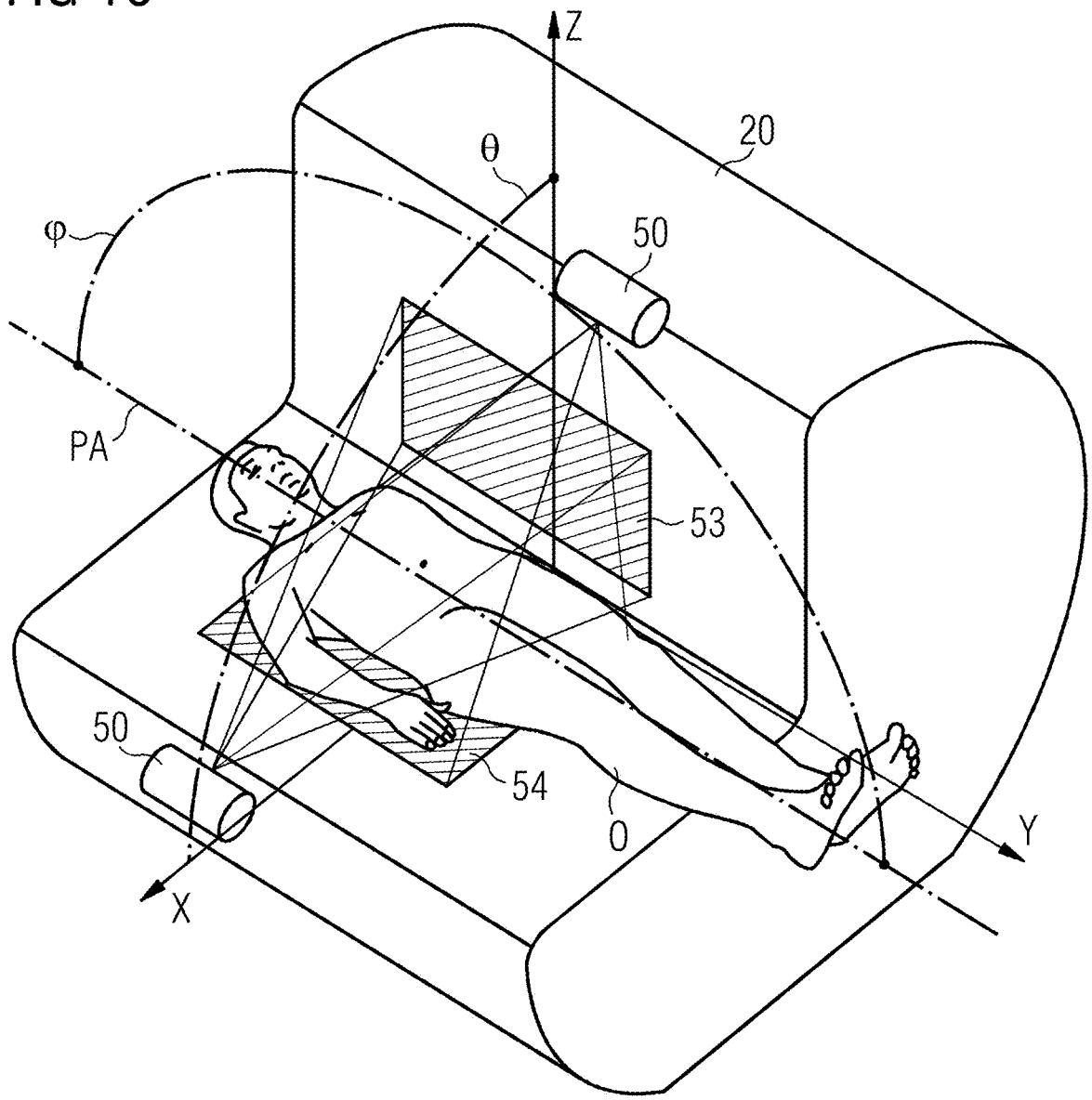
FIG. 16 shows an AMR hybrid system using a "PacMan" MR-scanner according to an exemplary embodiment.

FIG. 16 shows an Angiographic Magnetic Resonance (AMR) hybrid system using a "PacMan" MR-scanner 20 that can be used for interventional radiology applications. The above described "PacMan" MR-scanner 20 (see e.g. FIGS. 11 and 12) is used to generate real-time MR images of soft tissues that are to be fused together with X-ray images collected at two digital X-ray detectors 53, 54, as the patient body (the object O) is exposed to the X-ray beam emerging out of the X-ray tube (radiation source 50).

The patient O lies on a patient table 8 (not shown in this figure but similar to the one shown in FIG. 11). The patient table 8 has at least one or preferably multiple degrees of freedom in motion (e.g. vertically, horizontally and/or rotating around a vertical axis). Moreover, the X-ray source also can be moved at various positions and respective angulations. The X-ray source can move along a 90° θ-path by rotating around a longitudinal patient axis PA and further along a 180° φ-path by rotation around the X-axis of the system. This allows for much better freedom in the generation of the 2D projection images recorded at the detectors 53, 54 and for elaborating of a high-quality treatment plan in challenging clinical cases by using e.g. stereotactic X-ray radiology.

In a further inventive step, multiple X-ray projection images acquired at various angulations (view angles) can be used by means of the method known as digital tomosynthesis to generate CT-like slice images through the patient body. Digital tomosynthesis is a method for performing high-resolution limited-angle tomography at radiation dose levels comparable with projection radiography. Tomosynthesis image reconstruction delivers slice images by using algorithms similar to CT reconstruction. Due to partial data sampling (limited view angles) with very few projections, approximation algorithms have to be used. Filtered back-projection and iterative, expectation-maximization algorithms have both been used to reconstruct slice images. Reconstruction algorithms for tomosynthesis are different from those of conventional CT, because the conventional filtered backprojection algorithm requires a complete set of data. Iterative algorithms based upon expectation maximization are most commonly used. Manufacturers of such systems use off-the-shelf GPUs to perform this reconstruction in a few seconds.

Figure 17:
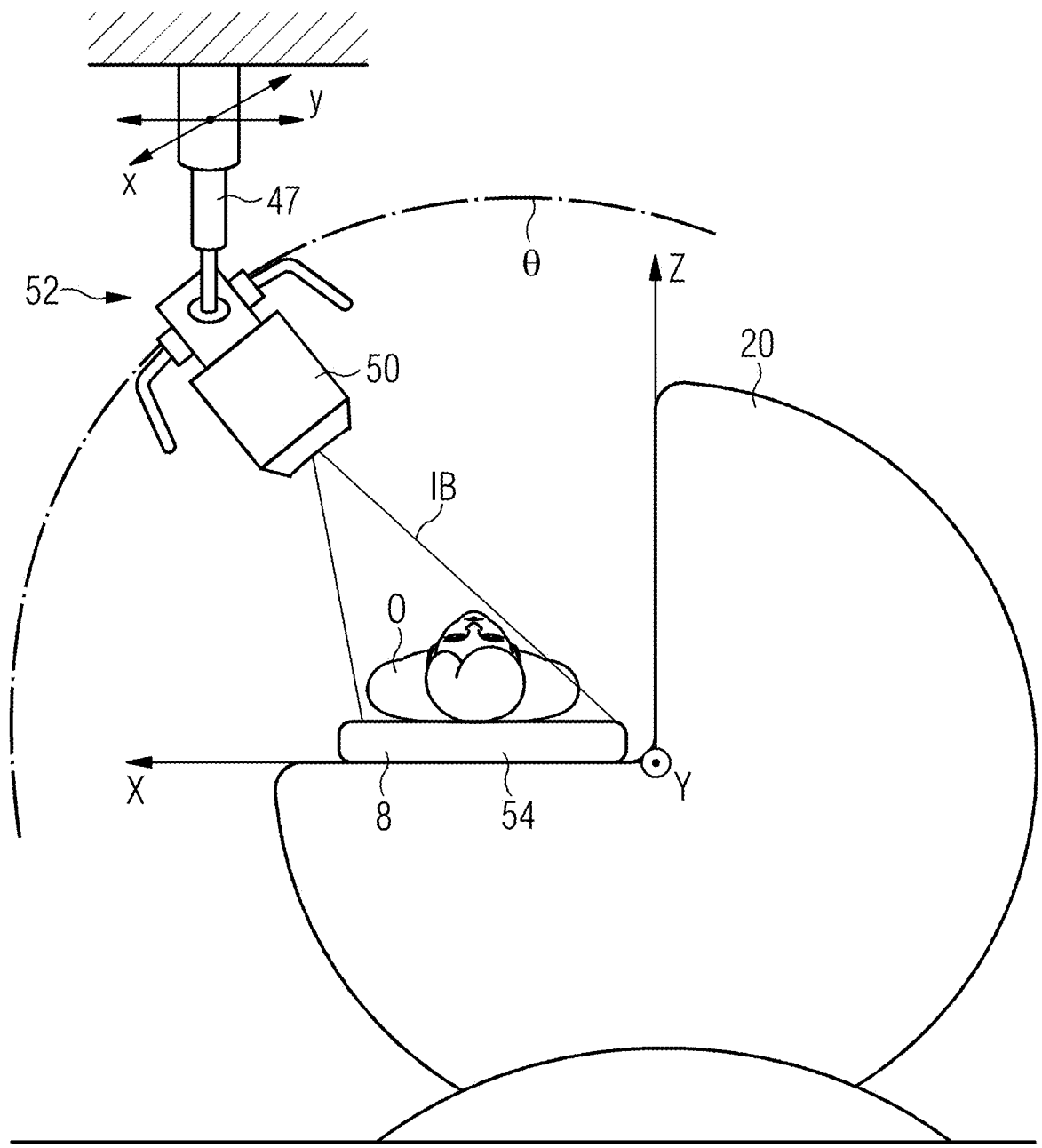
FIG. 17 shows an AMR hybrid system using a "PacMan" MR-scanner and an existing (available) X-ray robotic system according to an exemplary embodiment.

FIG. 17 shows an AMR hybrid system using a "Pac Man" MR-scanner 20 and an available X-ray robotic system. The new "PacMan" MR-scanner 20 is compatible and can be directly used with available and with traditional X-ray imaging systems.

The "PacMan" MR-scanner 20 hosts a patient table 8 with integrated X-ray detector 54 and preferably multiple degrees of freedom in motion. The X-ray equipment 52 emits the imaging beam IB toward the patient O on the table 8. The X-ray tube (radiation source 50) is mounted on a telescopic arm 47 that moves along rails mounted on the ceiling along the OX axis x and independently along the OY axis y. The X-ray tube 50 also rotates to adjust the angulation between the X-ray beam IB and the patient O. It should be noted that all these functions are already available with available X-ray equipment 52.

Furthermore, the "PacMan" MR-scanner 20 could be combined with other types of available X-ray equipment 52 that uses a robotic arm 47 to position an X-ray beam IB at various positions around the patient O. For example, if a breast cancer screen indicates an abnormality, a biopsy of the suspicious tissue will be taken for closer examination, which requires exquisite targeting of the suspicious tissue. A combination of MRI imaging and X-ray would locate the exact target. The robot then guides the biopsy needle holder with the lesion so that the doctor can insert a needle precisely.

Figure 18:
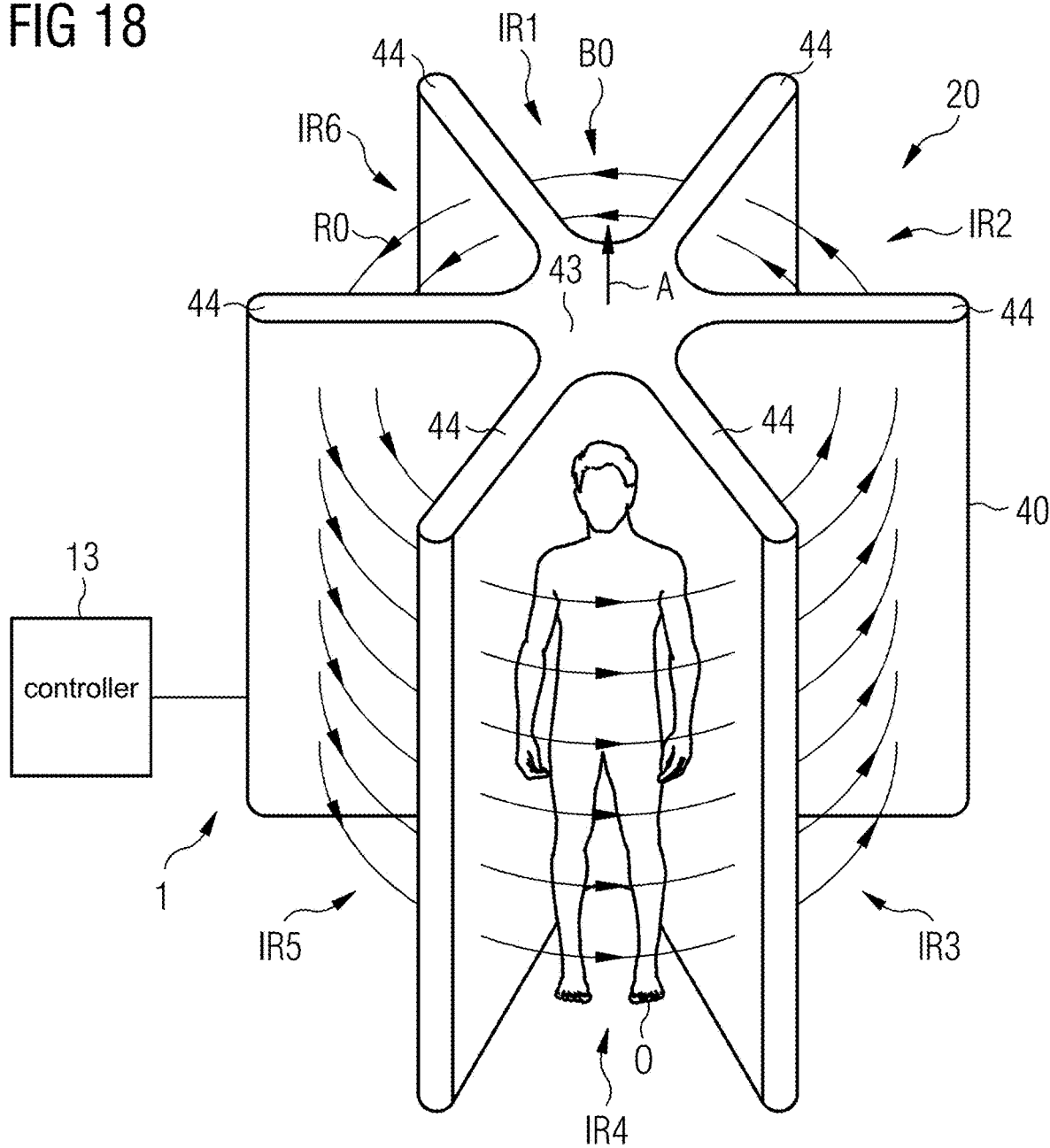
FIG. 18 shows an exemplary embodiment of a magnetic resonance tomography system with a star-shaped basic field magnet arrangement.

FIG. 18 shows an exemplary embodiment of a magnetic resonance tomography system 1 according to the disclosure with a star-shaped basic field magnet arrangement 40 around a central pillar 43 forming six imaging regions IR1, IR2, IR3, IR4, IR5, IR6.

Shown here is a magnetic resonance scanner 20, the function of which can be controlled by a controller 13. The controller 13 can in principle be constructed in a similar manner and have the same components as the controller 13 in a conventional MR system according to FIG. 1. Likewise, it can also have a suitable terminal or the like (which is not shown here).

The basic field magnet arrangement 40 of the magnetic resonance scanner 20 in this figure comprises six (here identical) basic field magnet segments 44, which in this embodiment are arranged in a star shape about a central axis A with a rotational symmetry of 60° (that is also the symmetry axis A of the toroidal field). The basic magnetic field B0 indicated by arrows has a basic field main direction R0, which runs in the form of a circle or a toroidal magnetic field.

Such an MRI scanner 20 with such basic field magnet arrangement 40 permits measurements at six different imaging regions IR1, IR2, IR3, IR4, IR5, IR6, wherein a patient O could stand upright on vertical walls of the basic field magnet arrangement 40 (shown in imaging region IR4). Theoretically, measurements could take place simultaneously at all six imaging regions IR1, IR2, IR3, IR4, IR5, IR6. A central pillar 43 holds the basic field magnet segments 44 in place and may also comprise technical components, such as e.g. the electrical connections or even the power supply.

Of course, a magnetic resonance scanner 2 may also have more than six imaging regions IR1, IR2, IR3, IR4, IR5, IR6, its height may be lower, or it may be designed for examining small areas of the body, e.g. for head examinations or examinations of the extremities, the female breast, the prostate, the liver, kidneys or other organs. The star-shaped basic field magnet arrangement 40 could also be positioned lying.

Figure 19:
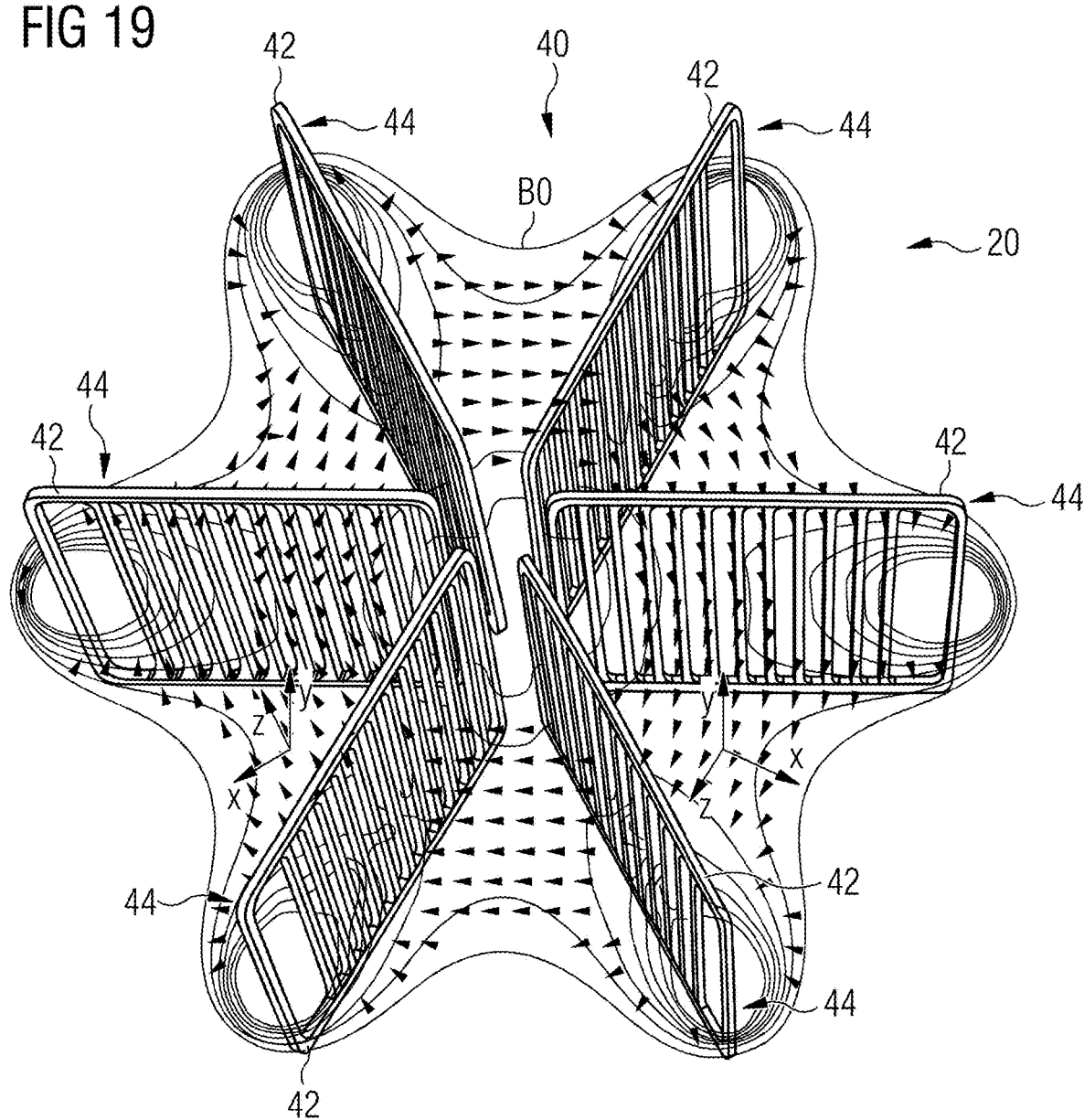
FIG. 19 shows the magnetic coils of a star-shaped basic field magnet arrangement according to an exemplary embodiment.

FIG. 19 shows the magnetic coils (the basic magnetic field segments 44) of a star-shaped basic field magnet arrangement 40. It is similar to FIG. 2 and shows a detailed schematic representation of the individual basic field magnet segments 44 of a star-shaped basic field magnet arrangement 40. Six coil-arrangements 42 can be seen here forming basic field magnet segments 44 of the basic field magnet arrangement 40. It should be noted that the lines of the basic magnetic field B0 doesn't form circles, but hexagonal contours extending over the six imaging regions IR1, IR2, IR3, IR4, IR5, IR6. In each imaging region, the field lines of the basic magnetic field B0 form parallel lines.

This "six-pack" toroidal MRI-scanner 20 allows scanning up to six patients simultaneously in six imaging regions IR1, IR2, IR3, IR4, IR5, IR6 (examination areas). The homogeneity of the magnet field B0 is high enough for conducting conventional MR imaging sequences. This MRI scanner 20 is supposed to acquire raw data and to reconstruct MR images by acquisition and image reconstruction methods as explained in the course of FIG. 1.

For each imaging region IR1, IR2, IR3, IR4, IR5, IR6 there is a local coordinate system XYZ associated therewith as exemplary depicted here only for two imaging regions IR1, IR2, IR3, IR4, IR5, IR6. Again, the local Z-axis is running parallel to and pointing in the same direction with the static basic magnetic field B0. The Y-axis is parallel to the rotational symmetry axis A (see FIG. 18) of the six-pack magnet system, while the X-axis corresponds to the radial direction pointing from the center of symmetry outwards from the magnet.

Arrows and iso-lines depict the overall distribution of the static basic magnetic field B0 within a cross sectional planar cut through the middle of the magnet. The local magnetic field vectors depicted by small arrows show the distribution of the local magnetic field magnitude (arrow size) and its direction (arrow orientation).

A significant advantage of such a symmetrical arrangement is the structural stability when the basic magnetic field B0 is switched on. The magnetic forces between the individual basic field magnetic segments 44 cancel each other out in the direction of the main magnetic field direction R0. Each basic field magnet segment 44 is attracted by its two neighbors, each with the same force. The resulting forces act inwardly towards the pillar 43 and can be compensated there very well by appropriate structural reinforcements.

Figure 20:
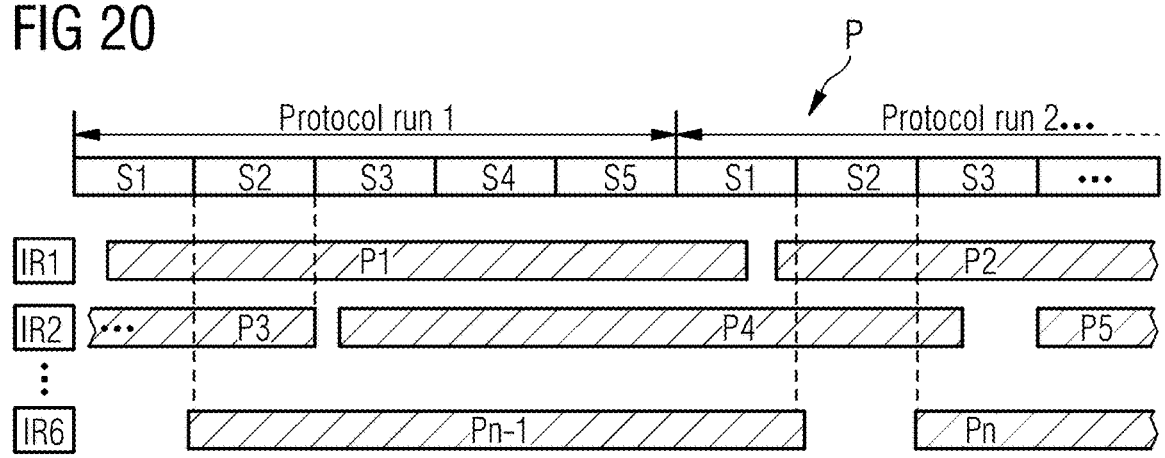
FIG. 20 shows a protocol for a parallel operation for a six-pack MRI scanner with six imaging regions all operated synchronously according to an exemplary embodiment.

FIG. 20 shows a (cyclically running) imaging protocol P for a parallel operation for a six-pack MRI scanner 20 (as e.g. shown in FIG. 19) with six imaging regions IR1, IR2, IR3, IR4, IR5, IR6 all operated synchronously. This exemplary embodiment of the inventive solution can be used for a parallel MRI scanner 20 having said six imaging regions IR1, IR2, IR3, IR4, IR5, IR6.

This operation mode is e.g. advantageous for scanning many patients for the same clinical indication or for screening numerous patients for a certain disease. For example, all patients may have a clinical indication for breast cancer screening, or all patients need a follow-up examination for prostate disease. In these cases, a conventional MRI scanner is supposed to run a so-called standardized imaging protocol P that consists in a succession of a few separate scans S1, S2, S3, S4, S5 conducted by using an MR imaging sequence with predefined imaging parameters that provides the specific image contrast.

For example, a prostate follow-up protocol may consist in a T1-weighted scan S1, followed by a T2-weighted scan S2, followed by a diffusion-weighted imaging scan S3, a contrast-agent-free perfusion imaging scan S4 and finally a spectroscopic MRI scan S5. Note that in this description an MRI scan and the time slots (for the scans S1, S2, S3, S4, S5 denote the same entity. An MR sequence is a temporal succession of RF-pulses and gradient pulses that repeats during the scan with various gradient amplitudes until all data needed to reconstruct an image has been acquired.

Figure 21:
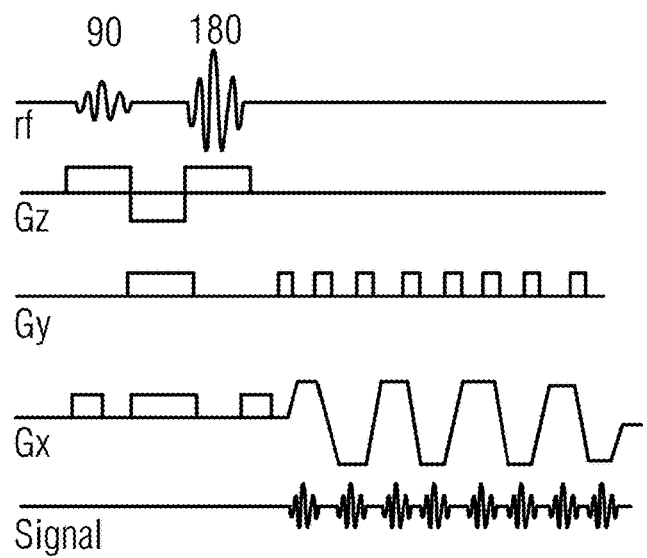
FIG. 21 shows an exemplary MR sequence that provides a diffusion-weighted contrast according to an exemplary embodiment.

An example conventional MR sequence is depicted by FIG. 21 that shows an exemplary MR sequence that provides a diffusion-weighted contrast. Not explicitly depicted by FIG. 20, every scan S1, S2, S3, S4, S5 typically consists of 128 repetitions of the same sequence and the associated signal measurements. The goal is to fill-up a data matrix generally having 128×128 data samples. This data matrix is further known in the art as the k-space. Usually 128 data samples that fill-in a full line into the k-space matrix are measured for each repetition of the MR sequence. In summary every time slot for a scan S1, S2, S3, S4, S5 in FIG. 20 consists in e.g. 128 repetition blocks of a sequence as the one depicted in FIG. 21, which fill-in all 128 lines into the k-space matrix. In this example the amplitude of the phase encoding gradient pulses Gy is set for each repetition in order to select the next k-space line to be acquired.

This inventive solution also relies on the fact that it is generally not important in which time-succession the k-space matrix is filled-up. Important is only that enough samples are available into this matrix allowing to reconstruct a full image. The main inventive idea is illustrated by FIG. 20. An exemplary parallel MRI scanner, having six imaging regions IR1, IR2, IR3, IR4, IR5, IR6 and being able to simultaneously scan up to six patients, cyclically runs a temporal succession of the same imaging protocol P (examination protocol). FIG. 20 shows the repetition of the same suit of MRI scans S1, S2, S3, S4, S5 used to investigate a cohort of patients P1, P2, P3, P4, P5 Pn−1, Pn for the same clinical indication. During a day there may be different imaging protocols P (MR protocols) to be run for another cohort of patients P1, P2, P3, P4, P5 Pn−1, Pn and for a different clinical indication. In each imaging region IR1, IR2, IR3, IR4, IR5, IR6 the scanner control system applies the same time succession of RF pulses and gradient pulses. In this way the risk of electromagnetic interferences between various imaging regions IR1, IR2, IR3, IR4, IR5, IR6 is minimized.

By a further inventive step, a patient can entry or exit an Imaging region IR1, IR2, IR3, IR4, IR5, IR6 at any point in time. There will be no deadlock or waiting time that would suspend the clinical workflow. A single technician or nurse would be able to assist every patient, to prepare the patient for the MR examination and to discharge the patient after the examination have been completed. By another inventive step, a patient may entry the imaging region IR1, IR2, IR3, IR4, IR5, IR6 even in the middle of a running scan S1, S2, S3, S4, S5.

As shown for a patient P1 of the cohort of patients P1, P2, P3, P4, P5, . . . , Pn−1, Pn in FIG. 20, this patient enters the imaging region IR1 at a point in time when the scanner is already running through the first half of scan S1. It means that only the second half of the k-space matrix will be acquired for the patient P1 with the MR sequence of scan S1.

Accordingly, patient P1 will complete the first run of the protocol and remain inside the scanner also during the second run of the protocol and at least until the completion of the first half of scan S1 in the second protocol run. By this way the k-space data matrix for scan S1 will be fully completed. Similar procedures apply for the other patients P2, P3, P4, P5, . . . , Pn−1, Pn. This inventive method is flexible enough to allow also for larger time gaps in between scanning two patients just in case one specific patient will require a longer preparation time. This may be the case for elderly patients with limited mobility, children or other special clinical cases. This is illustrated by the longer time gap between patient Pn−1 and Pn in imaging region IR6.

Figure 22:
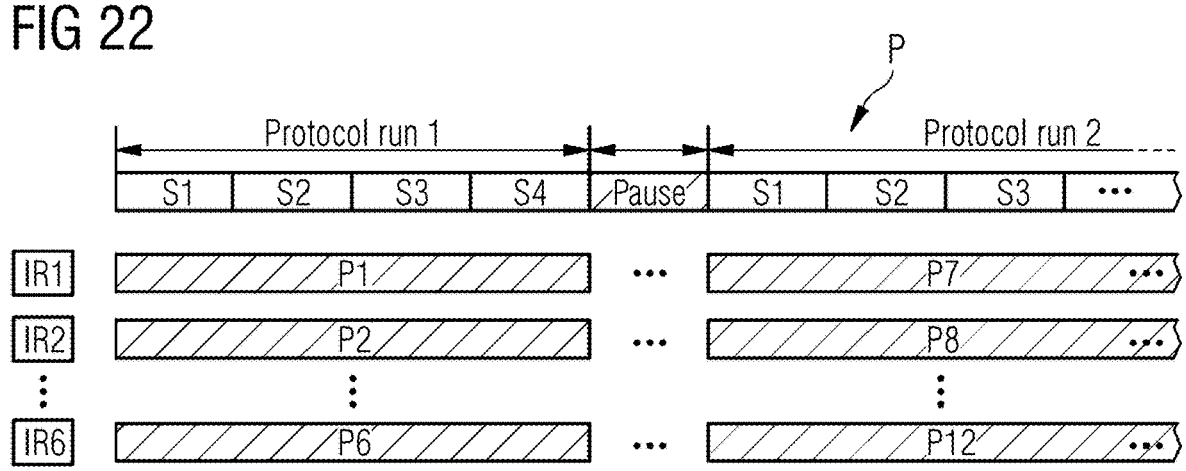
FIG. 22 shows a protocol for a parallel operation for a six-pack MRI scanner with all patients being examined synchronously according to an exemplary embodiment.

FIG. 22 shows an exemplary embodiment of the inventive solution in form of an imaging protocol P for a parallel operation for a "six-pack" MRI scanner 20 having six imaging regions IR1, IR2, IR3, IR4, IR5, IR6 (s. e.g. FIG. 18 or 19) with all patients in group one P1, P2, . . . , P6 and respectively all patients in group 2 P7, P8, . . . , P12 being examined (scanned) simultaneously.

There may be a clinical workflow advantage for investigating (scanning) a group of patients P1, P2, . . . , P6, P7, P8, P12 simultaneously with a pause in-between two protocol runs allowing for discharging and recharging the groups of patients P1, P2, . . . , P6, P7, P8, . . . , P12. This offers for example the opportunity for a nurse to prepare the whole group of patients together for the pending MR examination and to psychologically motivate the patients P1, P2, . . . , P6, P7, P8, . . . , P12 to keep together as a team and to bravely complete the MR examination up to the end.

This embodiment would provide a cheap solution for the problem many patients (predominately small children) have with MRI scanning by abandoning the scan before completion due to claustrophobic and/or anxious stress. One further advantage provided by a synchronous operation of a parallel MRI scanner 20 is that the acoustic noise generated in each imaging region IR1, IR2, IR3, IR4, IR5, IR6 is the same. Therefore, noise counteracting methods like e.g. active noise cancellation, noise beautification and the likes are much simpler to implement. Furthermore, the resulted noise acts less disturbing for the patients.

Although the present disclosure has been disclosed in the form of preferred embodiments and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "device" or similar designations does not preclude the use of more than one unit or device.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A magnetic resonance imaging system comprising:
a basic field magnetic arrangement configured to generate a main magnetic field and a number of spatially separated imaging regions, each of the spatially separated imaging regions of the basic field magnetic arrangement including at least two spatially separated magnet segments configured to generate respective segment magnetic fields with corresponding defined segment field directions, wherein:
the at least two of the spatially separated magnet segments are angularly arranged with respect to one another to form an opening angle therebetween, the at least two of the spatially separated magnet segments being configured such that the respective defined segment field directions of the at least two segment magnet segments run in an angular fashion with respect to one another such that the at least two segment magnetic fields result in the main magnetic field having a toroid form,
at least one imaging region of the spatially separated imaging regions is V-shaped and within the opening angle formed between the respective at least two of the spatially separated magnet segments arranged in a V-shaped arrangement, the at least one V-shaped imaging region being defined by the at least two of the spatially separated magnet segments arranged in the V-shaped arrangement, and
the magnetic resonance imaging system is adaptable to magnetic resonance (MR) imaging of dedicated body parts or organ parts of a patient.

2. The magnetic resonance imaging system according to claim 1, wherein the MRI system is adapted for:
cardiac imaging of a heart of the patient,
mammography imaging of a breast of the patient,
neurological imaging of a brain or spine of the patient,
urological imaging of a prostate of the patient,
orthopedics imaging of joints of the patient,
ophthalmologic imaging of an eye of the patient,
dental imaging of a jaw or teeth of the patient,
MR-guided radiation therapy, and/or
interventional radiology.

3. The magnetic resonance imaging system according to claim 1, wherein:
the at least two spatially separated magnet segments are aligned in a star-shaped fashion and the number of spatially separated imaging regions includes multiple imaging regions configured for simultaneous operation, and/or
a symmetry axis of the toroidal main magnetic field is positioned horizontally.

4. The magnetic resonance imaging system according to claim 1, wherein:
the at least two spatially separated magnet segments are aligned in a star-shaped fashion and the number of spatially separated imaging regions includes multiple imaging regions configured for simultaneous operation, and
a symmetry axis of the toroidal main magnetic field is positioned horizontally.

5. The magnetic resonance imaging system according to claim 1, wherein:
an angular coverage of an imaging region, of the number of spatially separated imaging regions, lies between 60° and 90° degrees, and
the magnetic resonance imaging system further comprises a magnetic resonance imaging scanner having an axial extension along a symmetry axis, the axial extension being: between 15 cm and 30 cm when the magnetic resonance imaging scanner is a dental scanner, between 15 cm and 30 cm when the magnetic resonance imaging scanner is a prostate scanner, or between 30 cm and 60 cm when the magnetic resonance imaging scanner is configured for cardiac imaging.

6. The magnetic resonance imaging system according to claim 1, wherein:
the magnetic resonance imaging system is configured such that the patient can stand, sit, and/or lie on their back during imaging,
the magnetic resonance imaging system includes a toroidal magnetic resonance imaging scanner is configured to move towards the patient from the front with a hinge mechanism fixed to a ceiling of a treatment room, and/or
the patient is movable to an imaging region of the number of spatially separated imaging regions by moving a patient bed or chair accordingly, or the magnetic resonance imaging scanner is configured such that the patient can lie in a predefined position in the imaging region of the magnetic resonance imaging scanner, at least a region of the patient that is to be scanned resting in a center part of the basic field magnetic arrangement.

7. The magnetic resonance imaging system according to claim 1, wherein:
the magnetic resonance imaging system is configured such that a symmetry axis of the toroidal main magnetic field is positioned horizontally and one side wall of an imaging region, of the number of spatially separated imaging regions, is positioned in a horizontal plane,
the magnetic resonance imaging system comprises a patient bed arranged on the side wall in the horizontal plane, the patient bed being movable along a vertical direction and/or along a horizontal direction,
the number of spatially separated imaging regions of the magnetic resonance imaging system comprises one single imaging region or two imaging regions in a mirrored arrangement, such that there is a number of magnet segments between the imaging regions forming a wall between the imaging regions together with a housing of a scanner of the magnetic resonance imaging system.

8. The magnetic resonance imaging system according to claim 1, wherein:
the number of spatially separated imaging regions comprise a number of V-shaped imaging regions,
the magnetic resonance imaging system comprises a further medical imaging and/or intervention component including an X-ray component, a radiographic imaging device, a tomographic imaging device, and/or γ-ray or X-ray sources for radiation therapy, and
the magnetic resonance imaging system is configured for magnetic resonance guided radio therapy, including on-line image guidance for application of a local therapy.

9. The magnetic resonance imaging system according to claim 8, wherein:
the magnetic resonance imaging system is configured for intensity-modulated radiation therapy, and
the magnetic resonance imaging system comprises:
a number of computer-controlled linear accelerators (LINACs) and/or other γ-ray or X-ray sources arranged such that a beam can be led into at least one of the spatially separated imaging regions, and
a controller is configured such that images or other information taken by the magnetic resonance imaging system is usable to control the number of LINACs or other γ-ray or X-ray sources.

10. The magnetic resonance imaging system according to claim 8, wherein:
the magnetic resonance imaging system is configured for angiographic magnetic resonance, the magnetic resonance imaging system including a number of X-ray imaging units, each X-ray imaging unit including an X-ray source and a digital X-ray detector, and
the magnetic resonance imaging system is configured to perform a parallel acquisition of MR images and X-ray images.

11. The magnetic resonance imaging system according to claim 10, wherein:
the magnetic resonance imaging system is configured to acquire multiple X-ray projection images at various angulations and generate CT-like slice images based on the acquired multiple X-ray projection images used for digital tomosynthesis, and
the acquired multiple X-ray projection images are registered with MR images taken parallelly to the X-ray projection images.

12. The magnetic resonance imaging system according to claim 8, further comprising a radiation source configured to be movable to various positions and respective angulations, the radiation source being movable along a 90° path by rotating around a longitudinal patient axis and/or along a 180° path by rotation around an X-axis of the magnetic resonance imaging system, wherein the radiation source is positioned on a rotating arm configured to rotate around a system axis of the scanner to change an angulation between a beam and the patient.

13. A method for controlling a magnetic resonance imaging (MRI) system with two or more spatially separated imaging regions, the method comprising:
generating a main magnetic field in the two or more imaging regions, each of the two or more imaging regions being formed by spatially separated magnet segments angularly arranged with respect to one another to form an opening angle therebetween, wherein at least one imaging region is V-shaped and within the opening angle formed between respective spatially separated magnet segments arranged in a V-shaped arrangement, the at least one V-shaped imaging region being defined by the respective spatially separated magnet segments arranged in the V-shaped arrangement;
adapting an imaging protocol for simultaneous scanning of the at least two patients at the two or more imaging regions to reduce a required time for the simultaneous scanning and/or to reduce interferences between the simultaneous scanning at the two or more imaging regions, wherein the generated main magnetic field is commonly utilized for the two or more imaging regions; and
applying the imaging protocol to the magnetic resonance imaging system.

14. The method according to claim 13, wherein:
applying the imaging protocol comprises a succession of separate scans, the separate scans including T1-weighted scans, T2-weighted scans, diffusion-weighted imaging scans, contrast agent-free perfusion imaging scans, and/or spectroscopic MRI scans; and
the method includes a temporal succession of the same imaging protocol cyclically running synchronously in every of the two or more imaging regions in a measurement cycle.

15. The method according to claim 13, wherein:
similar or identical sequences of scans are applied synchronously, while patients having an opportunity to be scanned asynchronously,
a first time of entrance of a first patient to a first imaging region of the two or more imaging regions is independent of a second time of entrance of a second patient in a second imaging region of the two or more imaging regions, and
a point of time when the first patient enters the first imaging region and an examination start time during a running imaging protocol is monitored relative to the running imaging protocol, and the examination of the first patient is ended when the point of time in a following imaging protocol is reached.

16. The method according to claim 13, wherein similar or identical sequences are applied synchronously, while a group of patients is scanned simultaneously and/or synchronously.

17. A computer program product, embodied on a non-transitory computer-readable storage medium, including a program and being directly loadable into a memory of the MRI system, when executed by a processor of the MRI system, causes the processor to perform the method as claimed in claim 13.

18. A non-transitory computer-readable storage medium with an executable program stored thereon, that when executed, instructs a processor to perform the method of claim 13.

* * * * *